(12) United States Patent
Stickeler et al.

(10) Patent No.: US 10,246,749 B2
(45) Date of Patent: Apr. 2, 2019

(54) METHOD FOR DIAGNOSING BREAST CANCER

(71) Applicant: Albert-Ludwigs-Universitaet Freiburg, Freiburg (DE)

(72) Inventors: Elmar Stickeler, Au (DE); Thalia Erbes, Gundelfingen (DE); Markus Jaeger, Ehrenkirchen (DE)

(73) Assignee: Albert-Ludwigs-Universitaet Freiburg, Freiburg (DE)

( * ) Notice: Subject to any disclaimer, the term of this patent is extended or adjusted under 35 U.S.C. 154(b) by 0 days.

(21) Appl. No.: 15/075,181

(22) Filed: Mar. 20, 2016

(65) Prior Publication Data

US 2016/0369352 A1    Dec. 22, 2016

(30) Foreign Application Priority Data

Mar. 20, 2015 (EP) .................... 15160154

(51) Int. Cl.
*C12Q 1/6886* (2018.01)

(52) U.S. Cl.
CPC ..... *C12Q 1/6886* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | | |
|---|---|---|---|---|
| 8,338,105 B2* | 12/2012 | Croce | ......... | C12Q 1/6809 435/6.14 |
| 8,518,647 B2* | 8/2013 | Croce | ......... | C12Q 1/6809 435/6.14 |
| 8,648,017 B2* | 2/2014 | Umansky | ......... | C12Q 1/6883 435/6.11 |
| 8,841,273 B2* | 9/2014 | Adam | ......... | C12N 15/1138 514/44 A |
| 9,309,559 B2* | 4/2016 | Loudig | ......... | C12O 1/6806 |
| 9,834,819 B2* | 12/2017 | Margulies | ......... | C12Q 1/6883 |
| 9,868,988 B2* | 1/2018 | Suthanthiran | ......... | C12Q 1/6883 |
| 2014/0178885 A1 | 6/2014 | Park | | |

FOREIGN PATENT DOCUMENTS

| | | |
|---|---|---|
| WO | WO 2008/029295 A2 | 3/2008 |
| WO | WO 2013/057567 A1 | 4/2013 |

OTHER PUBLICATIONS

Hanke, et al. (2010) A robust methodology to study urine microRNA as tumor marker:microRNA-126 and microRNA-182 are related to urinary bladder cancer. Urologic Oncology, V.28:655-61 (Year: 2010).*
Inman, et al. (2014) A pilot clinical trial of intravesical mitomycin-C and external deep pelvic hyperthermia for non-muscleinvasive bladder cancer. International Journal of Hyperthermia, v.30(3):171-5. (Year: 2014).*
Git, et al. (2010) "Systematic comparison of microarray profiling, real-time PCR, and next-generation sequencing technologies for measuring differential microRNA expression." RNA, v.16:991-1006. (Year: 2010).*
Erbes, et al. (2015) Feasibility of urinary microRNA detection in breast cancer patients and its potential as an innovative non-invasive biomarker. BMC Cancer, v.15:193. (Year: 2015).*
Di Leva, et al. (2013) "miRNA profiling of cancer." Current Opinion in Genetics & Development, v.23:3-11. (Year: 2013).*
Danila Serpico et al., "microRNAs in Breast Cancer Development and Treatment", *Cancer Treatment Reviews*, vol. 40, No. 5, p. 595-604, Jun. 1, 2014.
Thalia Erbes et al., "Feasibility of Urinary microRNA Detection in Breast Cancer Patients and Its Potential as an Innovative Non-Invasive Biomarker", *BMC Cancer*, vol. 15, No. 1, p. 193, Mar. 28, 2015.

* cited by examiner

*Primary Examiner* — Jennifer Pitrak McDonald
(74) *Attorney, Agent, or Firm* — Chalin A. Smith; Smith Patent, LLC

(57) ABSTRACT

The invention relates to a method of diagnosing breast cancer and to the use of biomarkers for the detection and diagnosis of breast cancer.

16 Claims, 15 Drawing Sheets
Specification includes a Sequence Listing.

miR-21 miR-155 miR-125b miR-451

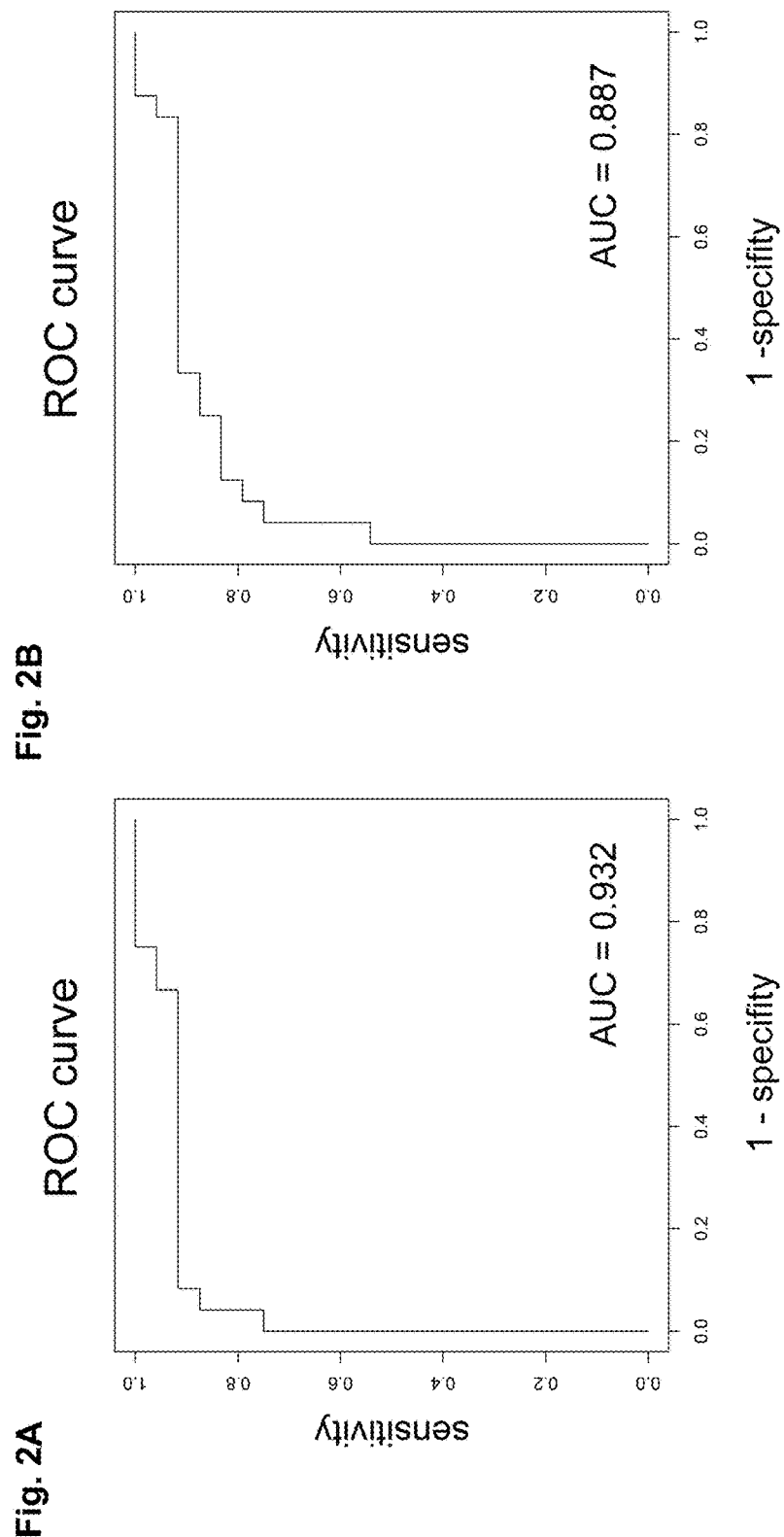

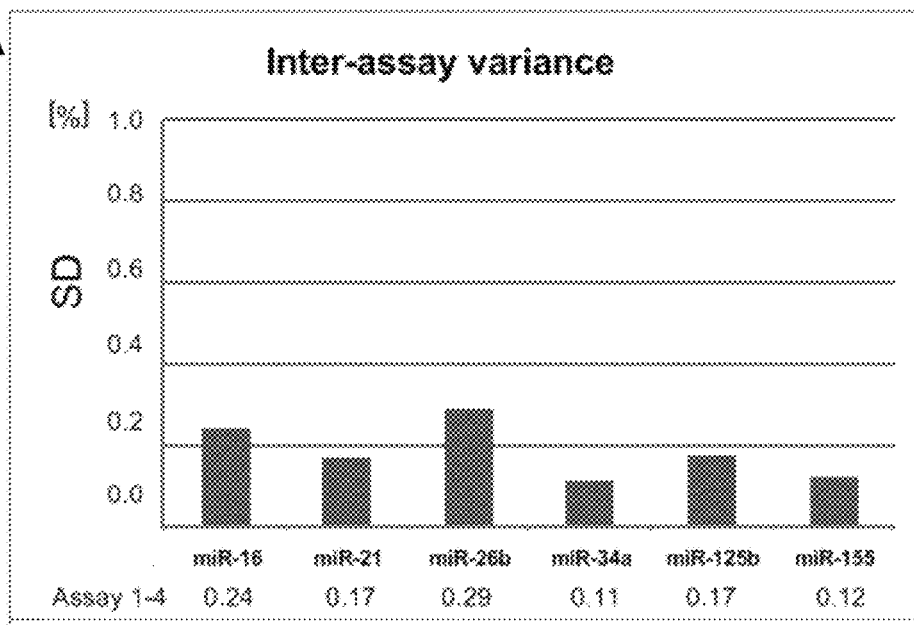
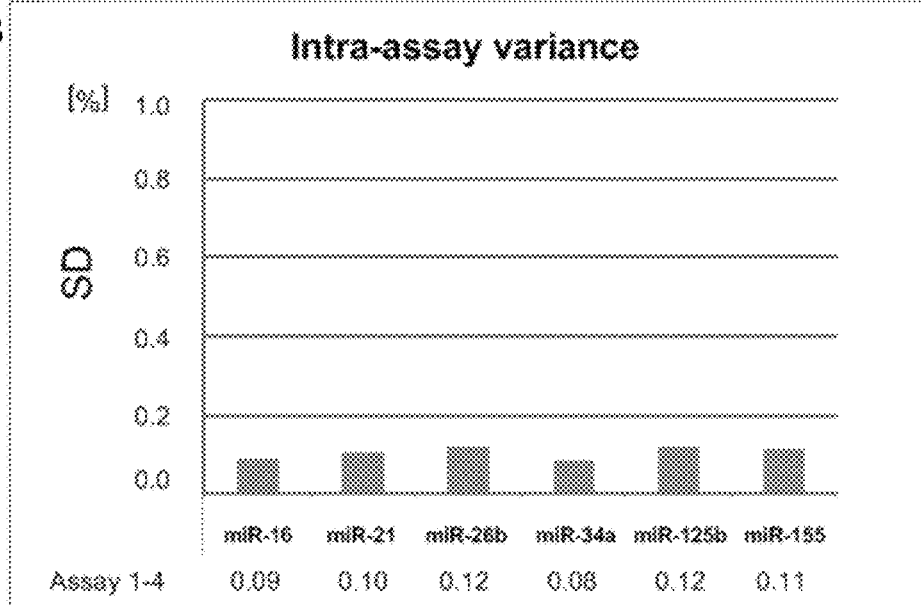

miR34a miR195

METHOD FOR DIAGNOSING BREAST CANCER

PRIORITY

This application claims priority to European Patent Application No. 15.160154.9, filed Mar. 20, 2015, the contents of which are incorporated by reference herein in its entirety.

SEQUENCE LISTING

The instant application contains a Sequence Listing that has been submitted in ASCII format via EFS-Web and is hereby incorporated by reference in its entirety. Said ASCII copy, created on Mar. 20, 2016, is named LNK_171 US_SequenceListing.txt and is 1,594 bytes in size.

BACKGROUND OF THE INVENTION

Small non-coding microRNAs (miRNAs, miRs) with a length of approximately 22 nucleotides are important post-transcriptional regulators of numerous human genes. MiRNAs modulate the expression of tumor suppressor genes as well as oncogenes [1-3]. In breast cancer (BC), emerging evidence suggests a potential role for deregulated miRNAs as modulators of carcinogenesis, proliferation, apoptosis and drug-resistance, respectively [4]. Most data exist for tumor tissue or breast cancer cell line-based miRNA expression profiles [5, 6]. However, there are numerous hypotheses for a pivotal role of miRNAs in intercellular communication [7, 8] partially based on the leakage of miRNAs in circulation [9] as well as by active and passive export mechanisms, respectively [9]. Recent studies documented the feasibility to detect stable miRNAs in serum and plasma. This opened the field for these circulating miRNAs as potential novel biomarkers in BC for early detection but also outcome prediction [10-13]. Our extensive literature research revealed the following nine miRNAs as actually relevant in BC, especially as potential blood based biomarker in discrimination BC from healthy controls or as predictors in therapy response (Table 1). For example, high expression serum levels of miR-10b, 34a and 155 were associated with primary metastatic BC (p<0.05) and high miR-34a levels correlated with an advanced stage of disease (p=0.01) [11]. Additional data revealed a strong correlation between serum miR-122 and miR-375 levels and neoadjuvant chemotherapy response in locally advanced BC [14]. Overexpression of miR-21 in BC tissue as well in blood based studies has a relevant oncogenic role by promoting invasion, proliferation and metastases and poor prognosis in BC patients [10, 15, 16]. Emerged studies showed up-regulated miR-125b serum levels in BC patients as an innovative serum biomarker for discrimination BC patients from healthy controls and to predict chemotherapeutic resistance [22, 23]. Other studies indicated miR-155 and miR-195 as promising diagnostic targets, while miR-155 is also discussed as a potential therapeutic target in BC [13, 17-20]. The role of miR-200 family in blocking tumor angiogenesis by inhibition epithelial-mesenchymal transition represents a potential relevant therapeutic predictive parameter in BC therapy [21, 22]. Most interestingly, in one study higher expression levels of miR-200b and miR-200c were observed in serum from circulating tumor cells (CTC)-positive metastatic BC patients compared to CTC-negative patients and promised miR-200b and miR-200c as an indicator for CTC-status and a prognostic marker in metastatic BC [23]. In regard of BC detection and discrimination from healthy controls miR-451 in combination with miR-145 were identified as the best potential circulating biomarker [24].

So far, urine, as an easy approachable compartment and a non-invasive source for circulating miRNAs, has not been tested in the setting of BC while current studies suggest a high potential of urinary miRNAs in urologic cancers [9].

SUMMARY OF THE INVENTION

The inventors investigated urine samples of breast cancer patients and surprisingly found that the urinary miRNAs miR-21, miR-125b, miR-375 and miR-451 displayed significant decreased expression levels in breast cancer patients compared to healthy controls. In addition, the urinary miRNA miR-155 showed an increased expression level in breast cancer patients. In particular, determination of the expression level of the four miRNAs miR-21, miR-125b, miR-155 and miR-451 in urine samples allows for a very specific discrimination between healthy individuals and BC patients.

The present invention therefore relates to the following embodiments.

[1] A method of diagnosing whether a subject has cancer (e.g. breast cancer), comprising determining the level of at least one miR gene product in a urine sample from the subject, wherein a decrease in the level of the miR gene product in the urine sample, relative to the level of a corresponding miR gene product in a control sample, is indicative of the subject having cancer, wherein the at least one miR gene product is selected from the group consisting of miR-21, miR-125b, miR-375, miR-451 and combinations thereof.

[2] The method of item [1], further comprising determining the level of miR-155 gene product in the urine sample from the subject, wherein an increase in the level of the miR-155 gene product in the urine sample, relative to the level of miR-155 gene product in the control sample, and a decrease in the level of the miR-21, miR-125b, and/or miR-451 gene product in the urine sample, relative to the level of a corresponding miR gene product in a control sample, is indicative of the subject having cancer.

[3] A method of diagnosing whether a subject has cancer (e.g. breast cancer), comprising
  a) determining in a urine sample from the subject a level of miR-21 gene product, miR-125b gene product, miR-375 gene product and/or miR-451 gene product,
  b) comparing the level of the miR-21 gene product in the urine sample to a control level of miR-21 gene product, comparing the level of the miR-125b gene product in the urine sample to a control level of miR-125b gene product, comparing the level of the miR-375 gene product in the urine sample to a control level of miR-375 gene product and/or comparing the level of miR-451 gene product in the urine sample to a control level of miR-451 gene product; and
  c) diagnosing whether the subject has cancer (e.g. breast cancer), wherein (i) a decrease in the level of miR-21 gene product in the urine sample, relative to the control level of miR-21 gene product, (ii) a decrease in the level of miR-125b gene product in the urine sample, relative to the control level of miR-125b gene product, (iii) a decrease in the level of miR-375 gene product in the urine sample, relative to the control level of miR-375 gene product, and/or (iv) a decrease in the level of miR-451 gene product in the urine sample, relative to the control level of miR-451 gene product, is indicative of the subject having cancer (e.g. breast cancer).

[4] The method of any one of the preceding items, comprising
  a) determining in the urine sample from the subject a level of miR-21 gene product, miR-125b gene product, and miR-451 gene product,
  b) comparing the level of the miR-21 gene product in the urine sample to a control level of miR-21 gene product, comparing the level of the miR-125b gene product in the urine sample to a control level of miR-125b gene product, and comparing the level of miR-451 gene product in the urine sample to a control level of miR-451 gene product; and
  c) diagnosing whether the subject has cancer (e.g. breast cancer), wherein (i) a decrease in the level of miR-21 gene product in the urine sample, relative to the control level of miR-21 gene product, (ii) a decrease in the level of miR-125b gene product in the urine sample, relative to the control level of miR-125b gene product, and (iii) a decrease in the level of miR-451 gene product in the urine sample, relative to the control level of miR-451 gene product, is indicative of the subject having cancer (e.g. breast cancer).

[5] The method of item [3] or [4], further comprising:
  a) determining in the urine sample from the subject a level of miR-155 gene product,
  b) comparing the level of the miR-155 gene product in the urine sample to a control level of miR-155 gene product, and
  c) diagnosing whether the subject has cancer (e.g. breast cancer), wherein an increase in the level of miR-155 gene product in the urine sample, relative to the control level of miR-155 gene product, is indicative of the subject having cancer (e.g. breast cancer).

[6] A method of diagnosing whether a subject has cancer (e.g. breast cancer), comprising:
  a) determining in a urine sample from the subject a level of miR-21 gene product, miR-125b gene product, miR-155 gene product and miR-451 gene product,
  b) comparing the level of the miR-21 gene product in the urine sample to a control level of miR-21 gene product, comparing the level of the miR-125b gene product in the urine sample to a control level of miR-125b gene product, comparing the level of the miR-155 gene product in the urine sample to a control level of miR-155 gene product and comparing the level of miR-451 gene product in the urine sample to a control level of miR-451 gene product; and
  c) diagnosing whether the subject has cancer (e.g. breast cancer), wherein (i) a decrease in the level of miR-21 gene product in the urine sample, relative to the control level of miR-21 gene product, (ii) a decrease in the level of miR-125b gene product in the urine sample, relative to the control level of miR-125b gene product, (iii) an increase in the level of miR-155 gene product in the urine sample, relative to the control level of miR-155 gene product, and (iv) a decrease in the level of miR-451 gene product in the urine sample, relative to the control level of miR-451 gene product, is indicative of the subject having cancer (e.g. breast cancer).

[7] The method of any one of the preceding items, wherein the control sample is a urine sample from one or more healthy individuals, preferably from one or more healthy women.

[8] The method of any one of the preceding items, wherein the subject is a female human.

[9] The method of any one of the preceding items, wherein the level of miR gene product(s) is measured by quantitative RT-PCR or by hybridisation using an oligonucleotide microarray.

[10] The method of any one of the preceding items, wherein said decrease in the level of gene product relative to the control level is at least 25%.

[11] A kit for the detection or diagnosis of cancer (e.g. breast cancer), comprising an oligonucleotide capable of hybridizing to a nucleic acid consisting of SEQ ID NO:1 or 2, an oligonucleotide capable of hybridizing to a nucleic acid consisting of SEQ ID NO:3, 4 or 9, and an oligonucleotide capable of hybridizing to a nucleic acid consisting of SEQ ID NO:5 or 6.

[12] The kit of item [10], further comprising an oligonucleotide capable of hybridizing to a nucleic acid consisting of SEQ ID NO:7 or 8.

[13] The use of an oligonucleotide capable of hybridizing to a nucleic acid consisting of SEQ ID NO:1 or 2, an oligonucleotide capable of hybridizing to a nucleic acid consisting of SEQ ID NO:3, 4 or 9, and/or an oligonucleotide capable of hybridizing to a nucleic acid consisting of SEQ ID NO:5 or 6 for the diagnosis of cancer (e.g. breast cancer), said use comprising contacting said oligonucleotide(s) with a urine sample.

[14] The use of item [13], further comprising contacting an oligonucleotide capable of hybridizing to a nucleic acid consisting of SEQ ID NO:7 or 8 with said urine sample.

[15] The kit or use of any one of items [11] to [14], wherein said oligonucleotide capable of hybridizing to a nucleic acid consisting of SEQ ID NO:1 or 2 is perfectly complementary to SEQ ID NO:2, the oligonucleotide capable of hybridizing to a nucleic acid consisting of SEQ ID NO:3, 4 or 9 is perfectly complementary to SEQ ID NO:4, and/or the oligonucleotide capable of hybridizing to a nucleic acid consisting of SEQ ID NO:5 or 6 is perfectly complementary to SEQ ID NO:6.

[16] The kit or use of any one of items [12], [14] or [15], wherein said oligonucleotide capable of hybridizing to a nucleic acid consisting of SEQ ID NO:7 or 8 is perfectly complementary to SEQ ID NO:8.

[17] The method, use or kit of any one of the preceding items, wherein the cancer is selected from the group consisting of breast carcinomas, lung carcinomas, gastric carcinomas, esophageal carcinomas, colorectal carcinomas, liver carcinomas, ovarian carcinomas, thecomas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as that associated with brain tumors), and Meigs' syndrome.

BRIEF DESCRIPTION OF THE DRAWINGS

FIGS. 2A and 2B: ROC (receiver operating characteristic) curve of (FIG. 2A) all miRNAs for the score combined from all miRNA (miR-21, miR-34a, miR-125b, miR-155, miR-195, miR-200b, miR-200c, miR-375, miR-451) in discrimination between BC patients and healthy controls. A combined ROC (receiver operating characteristic) curve of all miRNAs showed the excellent AUC (area under the curve) of 0.932 and a optimal sensitivity of 0.917 (95%-CI [0.812; 1.000]) and specificity of 0.917 (95%-CI [0.686; 0.978]), respectively. (FIG. 2B) ROC curve of the four significantly deregulated miRNAs (miR-21, miR-125b, miR-155, miR-451) was performed and showed high diagnostic accuracy with an AUC of 0.887 and a sensitivity of 0.833 (95%-CI [0.697; 0.997]) and specificity of 0.875 (95%-CI [0.640; 0.957]), respectively.

FIGS. 4A and 4B: Inter- and intra-assay variance in qPCR analysis in four assays (FIG. 4A): Inter-assay variance of miRNA types miR-16, -21, -26b, -34a, -125b, and -155

(FIG. 4B): Intra-assay variance of miRNA types miR-16, -21, -26b, -34a, -125b, and -155, showing mean standard deviation (SD) in percentage [%] as vertical-bar diagram with numerical values below.

DETAILED DESCRIPTION OF THE PREFERRED EMBODIMENTS

Figure 1A:
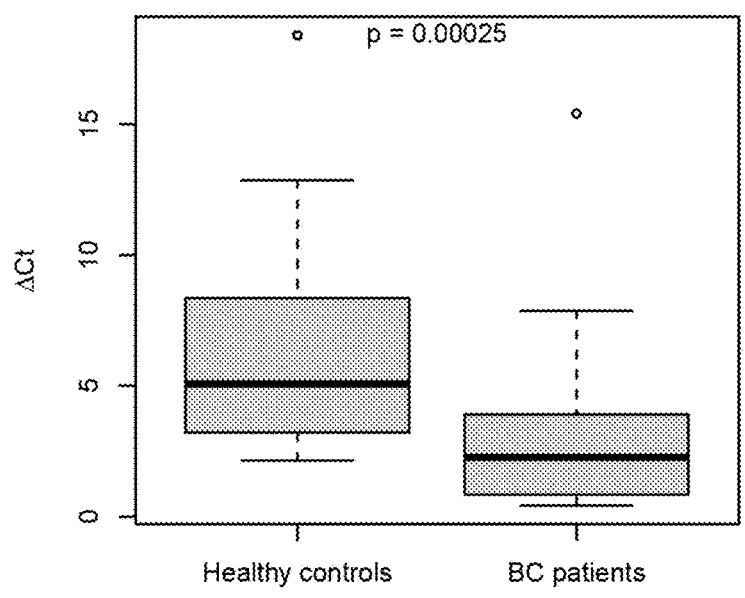
FIGS. 1A to 1D: Box plots A-D of ΔCt-values of significant urinary miRNAs in breast cancer patients compared to healthy controls Median urinary expression levels of miR-21 (2.27 vs. 5.07; $p<0.001$), miR-125b (0.72 vs. 1.62; $p<0.001$), and miR-451 (0.02 vs. 0.590; p=0.004) were significantly decreased in BC patients compared to healthy controls, respectively. Urinary miRNA-155 expression was significantly increased in BC patients compared to healthy controls (1.49 vs. 0.25; p<0.001). Median ΔCt-value and interquartile range of duplicate experiments. Thick lines: median (50% percentile); gray boxes: 25% to 75% percentile; thin lines: minimal and maximal value, °: moderate outlier. Mann Withney-U test. Quantitative realtime-PCR.
Figure 1B:
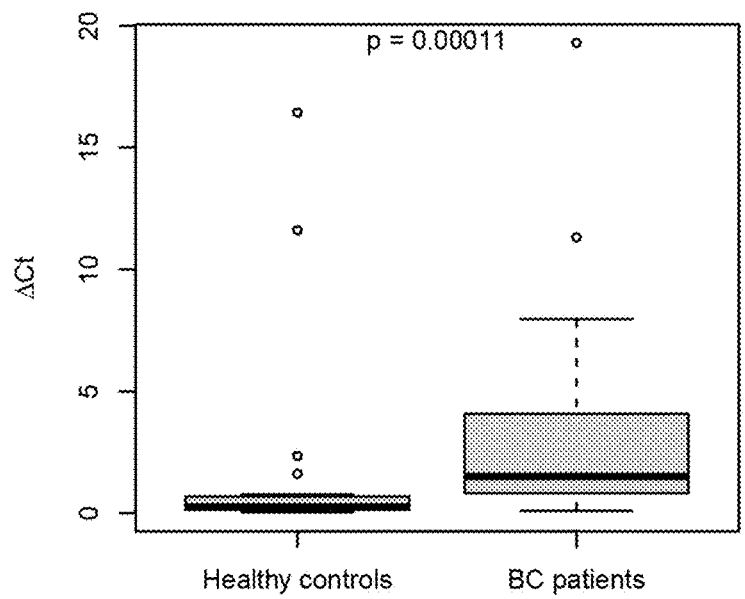
Figure 1C:
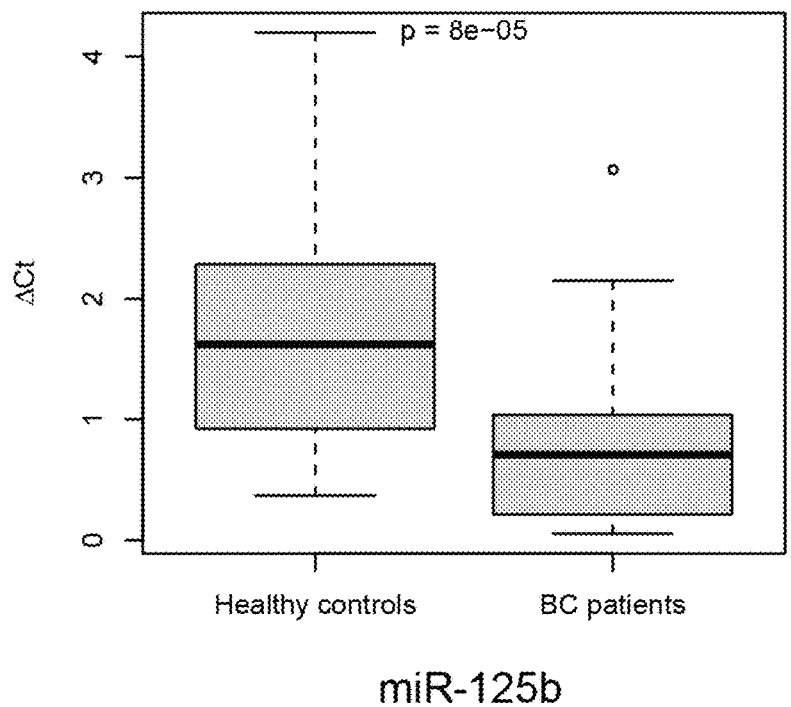
Figure 1D:
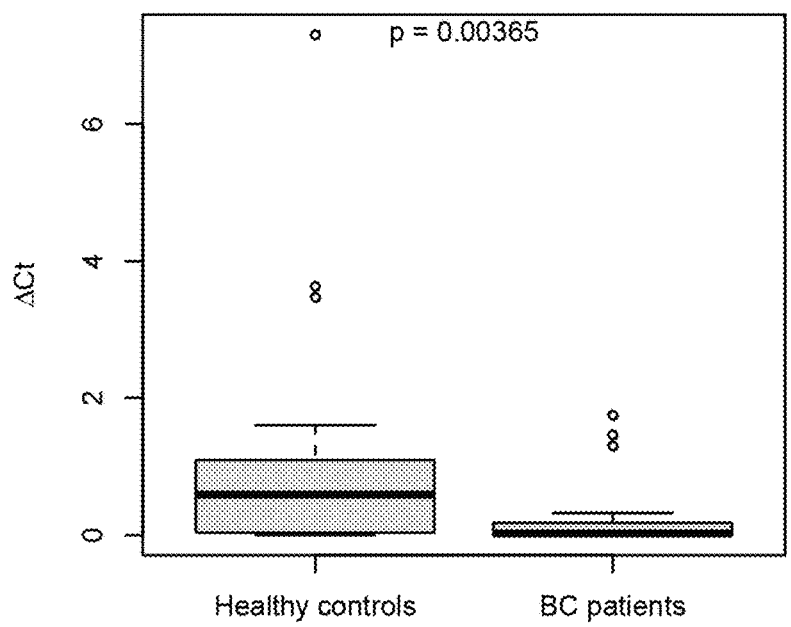
Figure 3A:
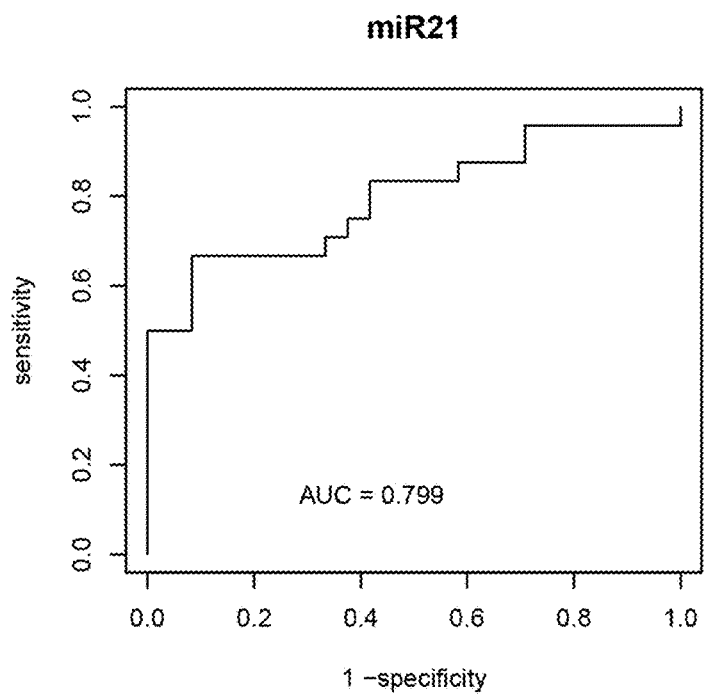
FIGS. 3A to 3I: ROC curves A-I of the diagnostic potential of the individual urinary miRNAs (miR-21, miR-34a, miR-125b, miR-155, miR-195, miR-200b, miR-200c, miR-375, miR-451) in discrimination between BC patients and healthy controls. The AUC values ranged from 0.502 to 0.819, respectively.
Figure 3B:
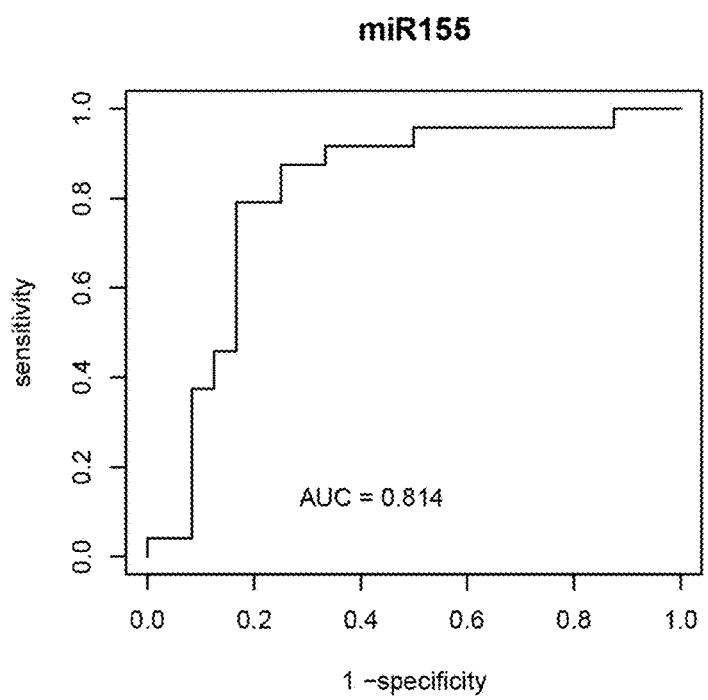
Figure 3C:
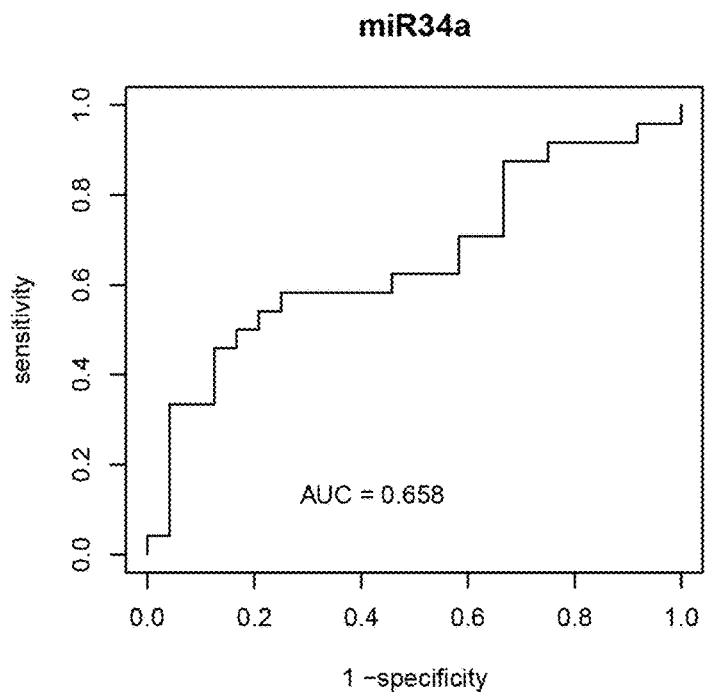
Figure 3D:
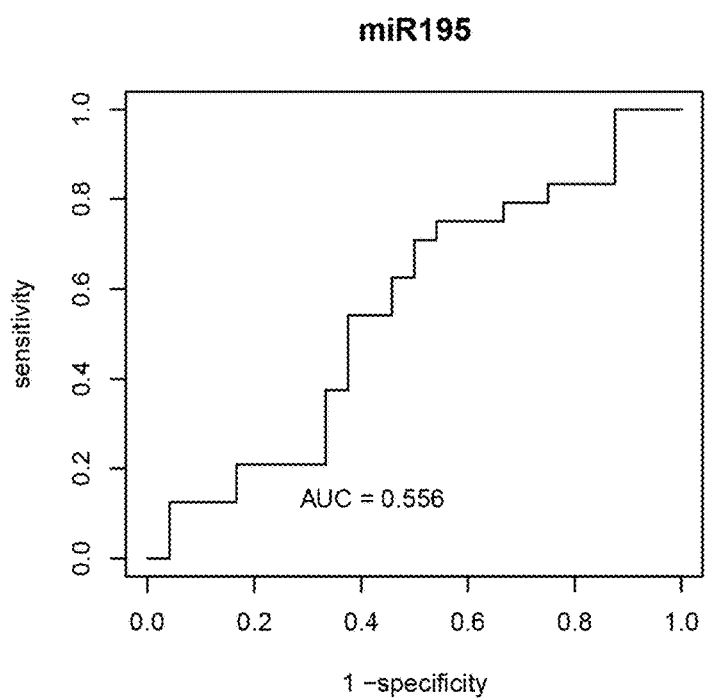
Figure 3E:
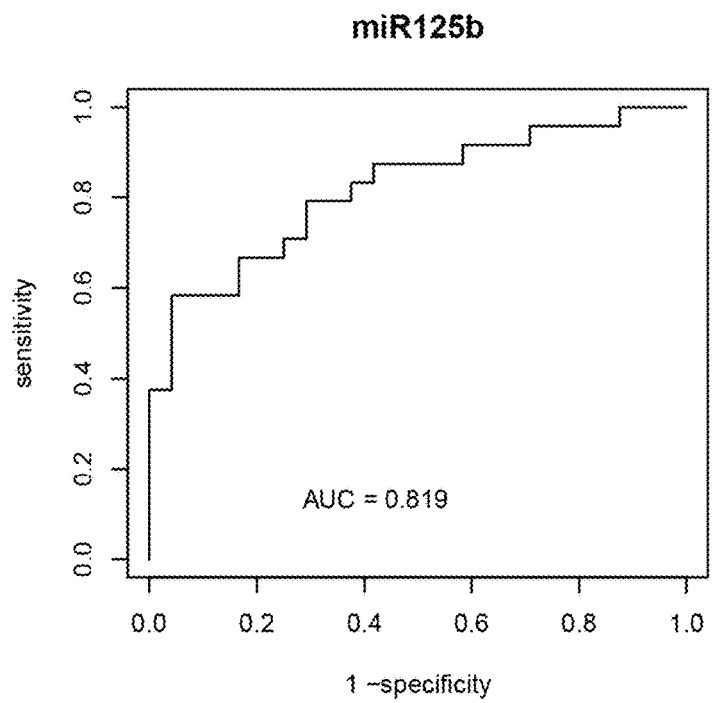
Figure 3F:
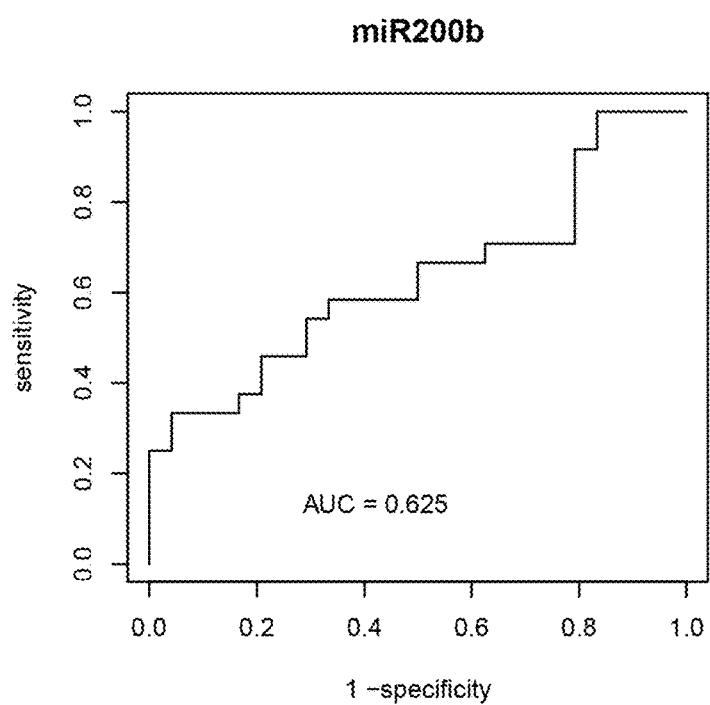
Figure 3G:
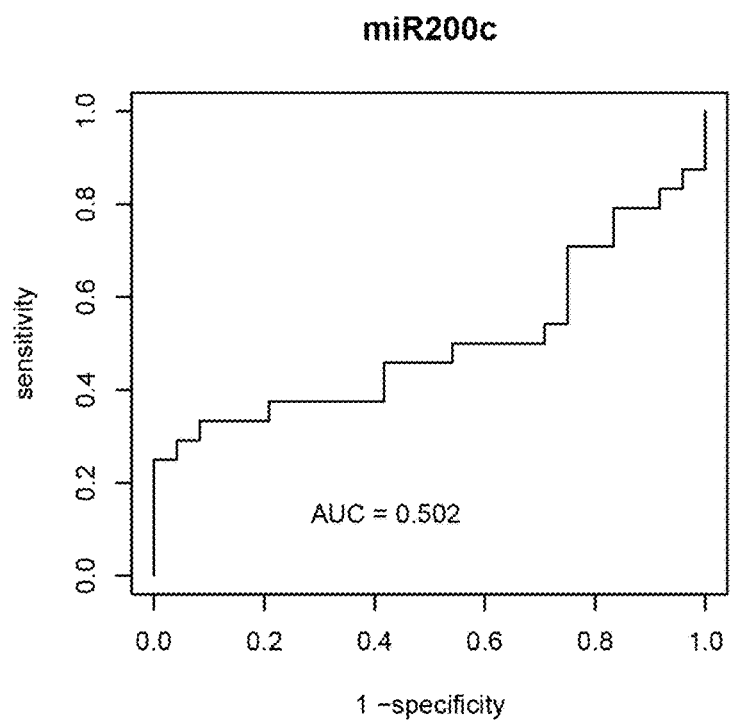
Figure 3H:
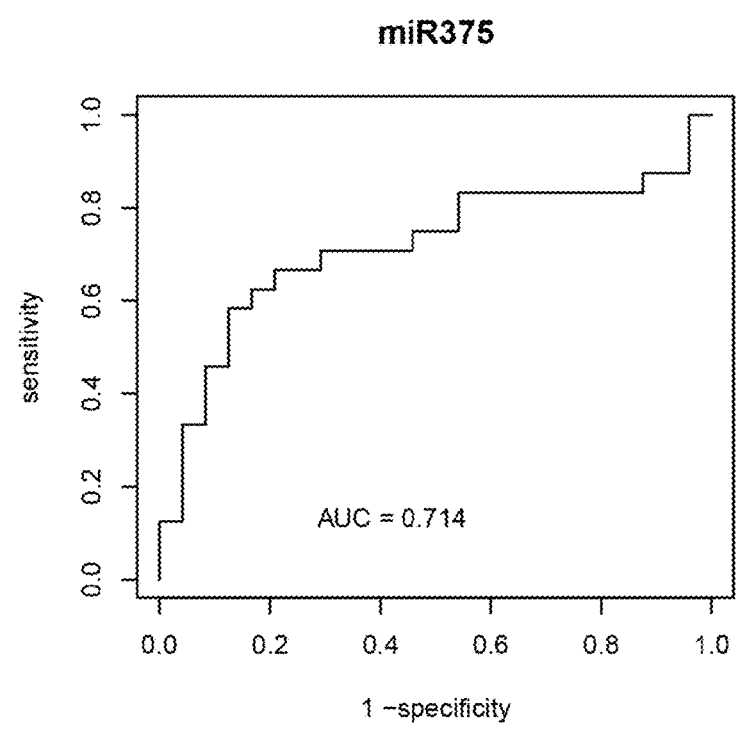
Figure 3I:
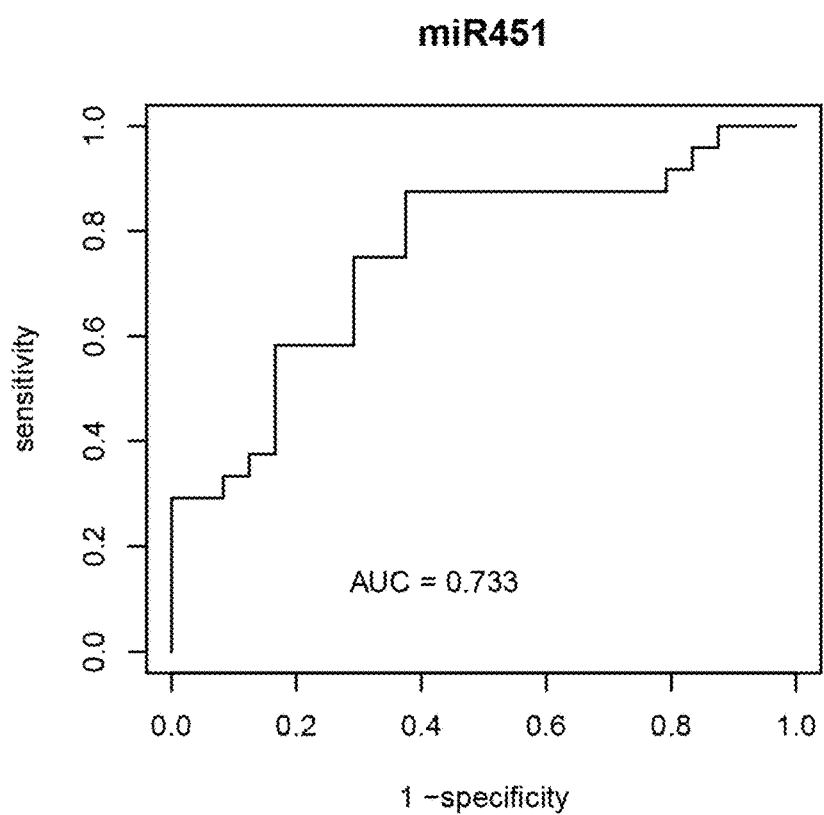

The present invention encompasses methods of diagnosing whether a subject has, or is at risk for developing, breast cancer, comprising determining the level of at least one miR gene product in a urine sample from the subject and comparing the level of the miR gene product in the urine sample to the level of a corresponding miR gene product in a control sample.

In particular, the invention relates to a method of diagnosing whether a subject has cancer (e.g. breast cancer), comprising determining the level of at least one miR gene product in a urine sample from the subject, wherein a decrease in the level of the miR gene product in the urine sample, relative to the level of a corresponding miR gene product in a control sample, is indicative of the subject having cancer (e.g. breast cancer), wherein the at least one miR gene product is selected from the group consisting of miR-21, miR-125b, miR-375, miR-451 and combinations thereof.

As used herein interchangeably, a "miR gene product," "microRNA," "miR," or "miRNA" refers to the unprocessed (e.g., precursor) or processed (e.g., mature) RNA transcript from a miR gene. As the miR gene products are not translated into protein, the term "miR gene products" does not include proteins. The unprocessed miR gene transcript is also called a "miR precursor" or "miR prec" and typically comprises an RNA transcript of about 70-100 nucleotides in length. The miR precursor can be processed by digestion with an RNAse (for example, Dicer, Argonaut, or RNAse III (e.g., *E. coli* RNAse III)) into an active 19-25 nucleotide RNA molecule. This active 19-25 nucleotide RNA molecule is also called the "processed" miR gene transcript or "mature" miRNA. The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having been processed from the miR precursor. When a microRNA is referred to herein by name, the name corresponds to both the precursor and mature forms, unless otherwise indicated. Table 1 depicts the nucleotide sequences of particular precursor and mature human microRNAs used in the present invention.

TABLE 1

| Name of microRNA | Precursor sequence | SEQ ID NO: of precursor sequence | Mature sequence | SEQ ID NO: of mature sequence |
|---|---|---|---|---|
| miR-21 | ugucgggua gcuuaucag acugauguu gacuguuga aucucaugg caacaccag ucgaugggc ugucugaca | 1 | uagcuuau cagacuga uguuga | 2 |
| miR-125b-1 | ugcgcuccu cucagucccc ugagacccu aacuuguga uguuuaccg uuuaaaucc acggguuag gcucuuggg agcugcgag ucgugcu | 3 | ucccugag acccuaac uuguga | 4 |

TABLE 1-continued

| Name of microRNA | Precursor sequence | SEQ ID NO: of precursor sequence | Mature sequence | SEQ ID NO: of mature sequence |
|---|---|---|---|---|
| miR-125b-2 | accagacuu uuccuaguc ccugagacc cuaacuugu gagguauuu uaguaacau cacaaguca ggcucuugg gaccuaggc ggagggga | 9 | ucccugag acccuaac uuguga | 4 |
| miR-451 | cuugggaau ggcaaggaa accguuacc auuacugag uuuaguaau gguaauggu ucucuugcu auacccaga | 5 | aaaccguu accauuac ugaguu | 6 |
| miR-155 | cuguuaaug cuaaucgug auaggggu uuugccucc aacugacuc cuacauauu agcauuaac ag | 7 | uuaaugcu aaucguga uaggggu | 8 |
| miR-375 | ccccgcgac gagccccuc gcacaaacc ggaccugag cguuuuguu cguucggcu cgcgugagg c | 10 | uuuguucg uucggcuc gcguga | 11 |

As used herein, a "subject" can be any mammal that has, or is suspected of having, breast cancer. In a preferred embodiment, the subject is a human who has, or is suspected of having, breast cancer. Most preferably, the subject is a female human, e.g. a woman at an age of 30 to 70 years, 35 to 69 years, 40 to 67 years, or 45 to 65 years.

The term "urine sample" refers to a sample which comprises or consists of urine. For determining the level of miR gene products in the urine sample, the urine sample is typically processed. The processing may include (but is not limited to) RNA isolation and/or purification, nucleic acid precipitation, dissolution of precipitated nucleic acid, concentration, dilution, and combinations thereof.

The level of at least one miR gene product is determined in a urine sample obtained from the subject. A corresponding control sample, which is also a urine sample, can be obtained from a healthy human individual or population of healthy individuals. The healthy "control" individual preferably has the same gender as the subject, and optionally a similar age (i.e. +/−10 years the age of the subject). Most preferably, the "control" individual is a healthy woman at an age of 30 to 70 years, 35 to 69 years, 40 to 67 years, or 45 to 65 years. The control urine sample is then processed along with the urine sample from the subject, so that the levels of miR gene product in the subject's urine sample can be compared to the corresponding miR gene product levels in the control sample. A reference miR expression standard for the urine sample can also be used as a control.

An alteration (e.g., an increase or decrease) in the level of a miR gene product in the sample obtained from the subject, relative to the level of a corresponding miR gene product in a control sample, as described below, is indicative of the presence of breast cancer in the subject. In one embodiment, the level of the at least one miR gene product in the test sample is greater than the level of the corresponding miR gene product in the control sample (i.e., expression of the miR gene product is "up-regulated"). As used herein, expression of a miR gene product is "up-regulated" when the amount of miR gene product in a urine sample from a subject is greater than the amount of the same gene product in a control sample. In another embodiment, the level of the at least one miR gene product in the urine sample is less than the level of the corresponding miR gene product in the control sample (i.e., expression of the miR gene product is "down-regulated"). As used herein, expression of a miR gene is "down-regulated" when the amount of miR gene product produced from that gene in a urine sample from a subject is less than the amount produced from the same gene in a control sample. The relative miR gene expression in the control and normal samples can be determined with respect to one or more RNA expression standards. The standards can comprise, for example, the urinary miR gene expression level in healthy subject, or the average level of urinary miR gene expression previously obtained for a population of healthy human controls. "Healthy" means that the subject or human controls do not have breast cancer or another type of cancer.

In one embodiment, the method comprises determining the level of a miR-21 gene product, wherein a decrease in the level of the miR-21 gene product in the urine sample, relative to the level of miR-21 gene product in a control sample, is indicative of the subject having breast cancer. The miR-21 gene product preferably is an RNA molecule comprising or consisting of SEQ ID NO:1 or 2, e.g. (i) an RNA molecule substantially consisting of SEQ ID NO:1, (ii) an RNA molecule which is a fragment of SEQ ID NO:1 wherein said fragment comprises SEQ ID NO:2, or (iii) an RNA molecule substantially consisting of SEQ ID NO:2.

In another embodiment, the method comprises determining the level of a miR-125b gene product, wherein a decrease in the level of the miR-125b gene product in the urine sample, relative to the level of miR-125b gene product in a control sample, is indicative of the subject having breast cancer. The miR-125b gene product preferably is an RNA molecule comprising or consisting of SEQ ID NO:3, 9 or 4, e.g. (i) an RNA molecule substantially consisting of SEQ ID NO:3 or 9, (ii) an RNA molecule which is a fragment of SEQ ID NO:3 or 9 wherein said fragment comprises SEQ ID NO:4, or (iii) an RNA molecule substantially consisting of SEQ ID NO:4.

In another embodiment, the method comprises determining the level of a miR-451 gene product, wherein a decrease in the level of the miR-451 gene product in the urine sample, relative to the level of miR-451 gene product in a control sample, is indicative of the subject having breast cancer. The miR-451 gene product preferably is an RNA molecule comprising or consisting of SEQ ID NO:5 or 6, e.g. (i) an RNA molecule substantially consisting of SEQ ID NO:5, (ii) an RNA molecule which is a fragment of SEQ ID NO:5 wherein said fragment comprises SEQ ID NO:6, or (iii) an RNA molecule substantially consisting of SEQ ID NO:6.

In another embodiment, the method comprises determining the level of a miR-155 gene product, wherein an increase in the level of the miR-155 gene product in the urine sample, relative to the level of miR-155 gene product in a control sample, is indicative of the subject having breast cancer. The miR-155 gene product preferably is an RNA molecule comprising or consisting of SEQ ID NO:7 or 8, e.g. (i) an RNA molecule substantially consisting of SEQ ID NO:7, (ii) an RNA molecule which is a fragment of SEQ ID NO:7 wherein said fragment comprises SEQ ID NO:8, or (iii) an RNA molecule substantially consisting of SEQ ID NO:8.

In another embodiment, the method comprises determining the level of a miR-375 gene product, wherein a decrease in the level of the miR-375 gene product in the urine sample, relative to the level of miR-375 gene product in a control sample, is indicative of the subject having breast cancer. The miR-375 gene product preferably is an RNA molecule comprising or consisting of SEQ ID NO:10 or 11, e.g. (i) an RNA molecule substantially consisting of SEQ ID NO:10, (ii) an RNA molecule which is a fragment of SEQ ID NO:10 wherein said fragment comprises SEQ ID NO:11, or (iii) an RNA molecule substantially consisting of SEQ ID NO:11.

In another embodiment, the method comprises determining the level of a miR-21 gene product and a miR-125b gene product, wherein a decrease in the levels of the miR-21 and miR-125b gene products in the urine sample, relative to the respective levels of the corresponding miR gene products in a control sample, is indicative of the subject having breast cancer.

In another embodiment, the method comprises determining the level of a miR-21 gene product and a miR-451 gene product, wherein a decrease in the levels of the miR-21 and miR-451 gene products in the urine sample, relative to the respective levels of the corresponding miR gene products in a control sample, is indicative of the subject having breast cancer.

In another embodiment, the method comprises determining the level of a miR-451 gene product and a miR-125b gene product, wherein a decrease in the levels of the miR-451 and miR-125b gene products in the urine sample, relative to the respective levels of the corresponding miR gene products in a control sample, is indicative of the subject having breast cancer.

In another embodiment, the method comprises determining the level of a miR-21 gene product, a miR-125b gene product, and a miR-451 gene product, wherein a decrease in the level of the miR-125b and miR-451 gene products in the urine sample, relative to the respective levels of the corresponding miR gene products in a control sample, is indicative of the subject having breast cancer.

In another embodiment, the method comprises determining the level of a miR-21 gene product and a miR-155 gene product, wherein a decrease in the level of the miR-21 gene product in the urine sample, relative to the level of the miR-21 gene product in a control sample, and an increase in the level of the miR-155 gene product in the urine sample, relative to the level of the miR-155 gene product in the control sample, is indicative of the subject having breast cancer.

In another embodiment, the method comprises determining the level of a miR-125b gene product and a miR-155 gene product, wherein a decrease in the level of the miR-125b gene product in the urine sample, relative to the level of the miR-125b gene product in a control sample, and an increase in the level of the miR-155 gene product in the urine sample, relative to the level of the miR-155 gene product in the control sample, is indicative of the subject having breast cancer.

In another embodiment, the method comprises determining the level of a miR-451 gene product and a miR-155 gene product, wherein a decrease in the level of the miR-451 gene product in the urine sample, relative to the level of the miR-451 gene product in a control sample, and an increase in the level of the miR-155 gene product in the urine sample, relative to the level of the miR-155 gene product in the control sample, is indicative of the subject having breast cancer.

In another embodiment, the method comprises determining the level of a miR-21 gene product, a miR-451 gene product and a miR-155 gene product, wherein a decrease in the levels of the miR-21 and miR-451 gene products in the urine sample, relative to the respective levels of the corresponding miR gene products in a control sample, and an increase in the level of the miR-155 gene product in the urine sample, relative to the level of the miR-155 gene product in the control sample, is indicative of the subject having breast cancer.

In another embodiment, the method comprises determining the level of a miR-21 gene product, a miR-125b gene product and a miR-155 gene product, wherein a decrease in the levels of the miR-21 and miR-125b gene products in the urine sample, relative to the respective levels of the corresponding miR gene products in a control sample, and an increase in the level of the miR-155 gene product in the urine sample, relative to the level of the miR-155 gene product in the control sample, is indicative of the subject having breast cancer.

In another embodiment, the method comprises determining the level of a miR-125b gene product, a miR-451 gene product and a miR-155 gene product, wherein a decrease in the levels of the miR-125b and miR-451 gene products in the urine sample, relative to the respective levels of the corresponding miR gene products in a control sample, and an increase in the level of the miR-155 gene product in the urine sample, relative to the level of the miR-155 gene product in the control sample, is indicative of the subject having breast cancer.

In another embodiment, the method comprises determining the level of a miR-21 gene product, a miR-125b gene product, a miR-451 gene product and a miR-155 gene product, wherein a decrease in the levels of the miR-21, mir-125b and miR-451 gene products in the urine sample, relative to the respective levels of the corresponding miR gene products in a control sample, and an increase in the level of the miR-155 gene product in the urine sample, relative to the level of the miR-155 gene product in the control sample, is indicative of the subject having breast cancer.

The level of a miR gene product in a urine sample can be measured using any technique that is suitable for detecting RNA expression levels in a urine sample. Nucleic acids can used be as probes or primers for embodiments involving nucleic acid hybridization. As such, they may be used to assess miRNA expression. The nucleotide sequences of the invention may be used for their ability to selectively form duplex molecules with complementary stretches of DNAs and/or RNAs or to provide primers for amplification of DNA or RNA from samples.

Reverse transcription (RT) of RNA to cDNA followed by quantitative PCR (RT-PCR) can be used to determine the relative concentrations of specific miRNA species. By determining that the concentration of a specific mRNA species varies, it is shown that the gene encoding the specific mRNA species is differentially expressed. Another method for amplification is ligase chain reaction ("LCR"). U.S. Pat. No. 4,883,750 describes a method similar to LCR for binding probe pairs to a target sequence. A method based on PCR™ and oligonucleotide ligase assay (OLA), disclosed in U.S.

Pat. No. 5,912,148, may also be used. Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Alternatively, an oligolibrary, in microchip format (i.e., a microarray), may be constructed containing a set of oligonucleotide probes that are specific for a set of miR genes. Using such a microarray, the expression level of multiple microRNAs in a urine sample can be determined by reverse transcribing the RNAs to generate a set of target oligodeoxynucleotides, and hybridizing them to probe the oligonucleotides on the microarray to generate a hybridization, or expression, profile. The hybridization profile of the test sample can then be compared to that of a control sample to determine which microRNAs have an altered expression level in breast cancer cells. As used herein, "probe oligonucleotide" or "probe oligodeoxynucleotide" refers to an oligonucleotide that is capable of hybridizing to a target oligonucleotide. "Target oligonucleotide" or "target oligodeoxynucleotide" refers to a molecule to be detected (e.g., via hybridization). By "miR-specific probe oligonucleotide" or "probe oligonucleotide specific for a miR" is meant a probe oligonucleotide that has a sequence selected to hybridize to a specific miR gene product, or to a reverse transcript of the specific miR gene product.

The method of the invention may further comprise the step of comparing the level of the miR gene product in the urine sample to a control level of the miR gene product (e.g. the level in a control sample), and diagnosing whether the subject has breast cancer, wherein a decrease or increase of miR gene product in the urine sample, relative to the control level of miR gene product is indicative of the subject having breast cancer.

Breast cancer is a cancer that starts in the breast, usually in the inner lining of the milk ducts or lobules. There are different types of breast cancer, with different stages (spread), aggressiveness, and genetic makeup. Breast cancer subtypes may be categorized on an immunohistochemical basis. The breast cancer to be diagnosed, detected, monitored or screened in accordance with this invention may be invasive ductal carcinoma, ductal carcinoma in situ, or invasive lobular carcinoma. Alternatively, BC may be classified on the basis of receptor status. In another embodiment, the breast cancer to be diagnosed, detected, monitored or screened in accordance with this invention may therefore be: "normal" BC (ER+, PR+, HER2+, cytokeratin 5/6+, and HER1+),
"luminal A" BC (ER+ and/or PR+, HER2−),
"luminal B" BC (ER+ and/or PR+, HER2+),
"triple-negative" BC (ER−, PR−, HER2−),
"HER2+/ER−" BC (ER−, PR−, and HER2+), or
"unclassified BC" (ER−, PR−, HER2−, cytokeratin 5/6−, and HER1−).

In the method of the invention, the level of miR-21 gene product, miR-125b gene product, and/or miR-451 gene product in the urine sample from the subject, relative to the control level of the corresponding miR gene product, may be decreased by at least 25% to be indicative of breast cancer, and/or the level of miR-155 gene product, in the urine sample from the subject, relative to the control level of miR-155 gene product, may be increased by at least 100% to be indicative of breast cancer. In another embodiment, the level of miR-21 gene product, miR-125b gene product, and miR-451 gene product in the urine sample from the subject, relative to the control level of the corresponding miR gene product, may be decreased by at least 40% to be indicative of breast cancer, and/or the level of miR-155 gene product, in the urine sample from the subject, relative to the control level of miR-155 gene product, may be increased by at least 200% to be indicative of breast cancer.

The subject may be diagnosed as having breast cancer if
  the level of miR-21 gene product in the urine sample from the subject is less than 80%, less than 70%, less than 60%, or less than 50% of the control level of miR-21 gene product (e.g. the level in the control sample);
  the level of miR-125b gene product in the urine sample from the subject is less than 80%, less than 70%, less than 60%, or less than 50% of the control level of miR-125b gene product (e.g. the level in the control sample);
  the level of miR-375 gene product in the urine sample from the subject is less than 80%, less than 70%, or less than 60%, of the control level of miR-375 gene product (e.g. the level in the control sample);
  the level of miR-451 gene product in the urine sample from the subject is less than 80%, less than 60%, less than 40%, or less than 20% of the control level of miR-451 gene product (e.g. the level in the control sample); or
  the level of miR-155 gene product in the urine sample from the subject is greater than 150%, greater than 200%, greater than 300%, or greater than 400% of the control level of miR-155 gene product (e.g. the level in the control sample).

In a particular embodiment, the subject is diagnosed as having breast cancer if
  the level of miR-21 gene product in the urine sample from the subject is less than 80%, less than 70%, less than 60%, or less than 50% of the control level of miR-21 gene product (e.g. the level in the control sample);
  the level of miR-125b gene product in the urine sample from the subject is less than 80%, less than 70%, less than 60%, or less than 50% of the control level of miR-125b gene product (e.g. the level in the control sample);
  the level of miR-451 gene product in the urine sample from the subject is less than 80%, less than 60%, less than 40%, or less than 20% of the control level of miR-451 gene product (e.g. the level in the control sample); and
  the level of miR-155 gene product in the urine sample from the subject is greater than 150%, greater than 200%, greater than 300%, or greater than 400% of the control level of miR-155 gene product (e.g. the level in the control sample).

In another aspect, the invention pertains to a diagnostic kit, or a microarray, comprising an oligonucleotide capable of hybridizing to a nucleic acid consisting of SEQ ID NO:1 or 2, an oligonucleotide capable of hybridizing to a nucleic acid consisting of SEQ ID NO:3, 4 or 9, and an oligonucleotide capable of hybridizing to a nucleic acid consisting of SEQ ID NO:5 or 6. The kit preferably further comprises an oligonucleotide capable of hybridizing to a nucleic acid consisting of SEQ ID NO:7 or 8. The kit may further comprise an oligonucleotide capable of hybridizing to a nucleic acid consisting of SEQ ID NO:10 or 11.

In yet another embodiment, the diagnostic kit or microarray comprises an oligonucleotide capable of hybridizing to a nucleic acid consisting of SEQ ID NO:2, an oligonucleotide capable of hybridizing to a nucleic acid consisting of SEQ ID NO:4, and an oligonucleotide capable of hybridizing to a nucleic acid consisting of SEQ ID NO:6. The kit preferably further comprises an oligonucleotide capable of hybridizing to a nucleic acid consisting of SEQ ID NO:8. The kit may further comprise an oligonucleotide capable of hybridizing to a nucleic acid consisting of SEQ ID NO:11.

As used herein, "capable of hybridizing" preferably refers to high stringency hybridization conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. High stringency conditions would include, for example, low salt and/or high temperature conditions, such as provided by 0.02-0.1 M NaCl, at temperatures of 50-70° C. (e.g. 0.05 M NaCl at 60° C.).

In yet another aspect, the invention relates to the use of an oligonucleotide capable of hybridizing to a nucleic acid consisting of SEQ ID NO:1 or 2, an oligonucleotide capable of hybridizing to a nucleic acid consisting of SEQ ID NO:3, 4 or 9, and/or an oligonucleotide capable of hybridizing to a nucleic acid consisting of SEQ ID NO:5 or 6 for the diagnosis of breast cancer comprising contacting said oligonucleotide(s) with a urine sample. The use preferably further comprises contacting an oligonucleotide capable of hybridizing to a nucleic acid consisting of SEQ ID NO:7 or 8 with said urine sample. The use may further comprises contacting an oligonucleotide capable of hybridizing to a nucleic acid consisting of SEQ ID NO:10 or 11 with said urine sample. The oligonucleotides may be immobilized on a microarray.

In particular embodiments of the kit or use described above, said oligonucleotide capable of hybridizing to a nucleic acid consisting of SEQ ID NO:1 or 2 is perfectly complementary to SEQ ID NO:2, the oligonucleotide capable of hybridizing to a nucleic acid consisting of SEQ ID NO:3, 4 or 9 is perfectly complementary to SEQ ID NO:4, and/or the oligonucleotide capable of hybridizing to a nucleic acid consisting of SEQ ID NO:5 or 6 is perfectly complementary to SEQ ID NO:6. Additionally, the oligonucleotide capable of hybridizing to a nucleic acid consisting of SEQ ID NO:7 or 8 may be perfectly complementary to SEQ ID NO:8. Additionally, the oligonucleotide capable of hybridizing to a nucleic acid consisting of SEQ ID NO:10 or 11 may be perfectly complementary to SEQ ID NO:11. As used herein the term "complementary" refers to the reverse complement, unless indicated otherwise.

This diagnostic kit can be used for breast screening, e.g. by identifying changes in urine miRNA levels in breast cancer patients compared to normal cancer-free individuals, in a control group. The kit may further be used for the prognosis and/or prediction of outcome, e.g. by identifying differences between patients with early or late stage cancers, as well as stratifying patients into molecular subtypes. This information can then aid in strategic planning of an individual patients therapeutic regimen. Further, the kit may be used for the monitoring of response to treatments, e.g. through serial urinary miRNA measurements; particularly in the neoadjuvant chemotherapy and metastatic disease settings.

The methods, uses and kits of the invention have been described above in connection with breast cancer. The invention is also applicable for the diagnosis, detection and/or screening of other cancer types, e.g. of breast carcinomas, lung carcinomas, gastric carcinomas, esophageal carcinomas, colorectal carcinomas, liver carcinomas, ovarian carcinomas, thecomas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as that associated with brain tumors), and/or Meigs' syndrome. The embodiments described above in connection with BC apply to theses other cancer types mutatis mutandis.

The following examples illustrate the invention and should not be understood as limiting the invention to the exemplified embodiments.

Examples

In this pilot study, we evaluated to our knowledge for the first time whether circulating urinary miRNA pattern might be applicable as potential biomarkers for BC detection. Therefore we assessed the expression of a distinct panel of BC associated miRNAs (miR-21, miR-34a, miR-125b, miR-155, miR-195, miR-200b, miR-200c, miR-375, miR-451, respectively) in female healthy controls in comparison to newly diagnosed, so far untreated BC patients.

Methods

Cohorts and Sampling

Midstream specimen of urine (MSU) were collected in a case-control cohort of 24 untreated patients, newly diagnosed with primary BC in the adjuvant setting and of 24 healthy female controls at the Department of Obstetrics and Gynecology, University Medical Center Freiburg. Exemplarily, serum samples of four consecutive patients and healthy controls were collected for a comparative analysis with corresponding urine specimen. The specimen of urine and serum were collected from healthy women confirmed not to have BC and no history of other (malignant) diseases or current inflammation. For all BC patients, distant metastasis was excluded by staging procedures according to the current national guidelines. The institutional ethical review board of the University of Freiburg, approved the investigation protocol (36/12). All patients and healthy controls involved, gave written informed consent for participation in this study. In table 2 the characteristics of the study population are summarized. All MSU specimen were centrifuged extensively to eradicate contamination with any urothelial or microbiological cell material. Supernatant was used for subsequent analysis. Samples were stored at −80° C. until further processing.

TABLE 2

Characteristics of breast cancer (BC) patients and healthy controls
Relevant characteristics of 24 BC patients
and 24 healthy controls are demonstrated.

|  | BC patients | healthy controls | p value |
|---|---|---|---|
| N | 24 | 24 |  |
| Median age, y | 54 | 52 | 0.070 |
| Histology |  |  |  |
| Invasive ductal | 22 |  |  |
| Invasive lobular | 2 |  |  |
| Tumor stage |  |  |  |
| pT1 | 13 |  |  |
| pT2 | 8 |  |  |
| pT3 | 3 |  |  |
| Nodal status |  |  |  |
| pN0 | 15 |  |  |
| pN1 | 5 |  |  |
| pN2 | 4 |  |  |
| Grading |  |  |  |
| G1 | 2 |  |  |
| G2 | 13 |  |  |
| G3 | 9 |  |  |
| Hormone receptor status |  |  |  |
| ER positive | 22 |  |  |
| PR positive | 20 |  |  |
| HER2neu status |  |  |  |
| Positive | 2 |  |  |
| Mastectomy |  |  |  |
| Yes | 4 |  |  |
| No | 20 |  |  |

Statistical Analysis

The statistical analyses were performed by using the SPSS software package, version 22.0 (SPSS Inc. Chicago, Ill., USA) and the open available statistical software environment R (R Development Core Team, "R: A Language and Environment for Statistical Computing". R foundation for Statistical Computing, 2013. URL http://www.R-project.org). Mann Whitney-U test was applied to test the median urinary expression levels of miR-21, miR-34a, miR-125b, miR-155, miR-195, miR-200b, miR-200c, miR-375, and miR-451, respectively. Logistic regression was used to combine all miRNAs to a score which is interpreted as a diagnostic marker for discrimination of cases and controls. Its accuracy was investigated by an ROC (receiver operating characteristic) curve, the area under the curve (AUC) and accuracy measures for a suitable cut-off value.

RNA Isolation

Norgen's Urine microRNA Purification Kit (#29000, Norgen Biotek Corporation, Thorold, ON, Canada) was applied for isolation and purification of small RNA molecules (<200 nt). According to the manufacturer's protocol 1 ml urine per sample was lysed and RNA was isolated and purified in a spin column procedure. Serum samples were diluted 1:1 with water (RNAse-free, DEPC treated) to lower protein load before parallel RNA isolation with Norgen's kit. Purified miRNA was finally collected in 50 µl RNA Elution buffer (Kit component) and RNA concentration determined densitometrically using Eppendorf Biophotometer (Eppendorf, Hamburg, Germany). All miRNA samples were stored at −80° C.

Reverse Transcription

Generation of miRNA-cDNA was performed by Reverse Transcription of 250 ng miRNA/sample applying Megaplex™ Primer Pools, Human Pools A v2.1 (#4401009, Applied Biosystems®, Life Technologies™, Thermo Fischer Scientific Inc., Schwerte, Germany) in a total reaction volume of 20 µl. cDNA probes were stored at 4° C.

Pre-Amplification

Enhancement of miRNA-cDNA quantity was achieved by application of Megaplex™ PreAmp Primers, Human Pool A (#4399233, Applied Biosystems®). Thereto 5 µl of miRNA-cDNA generated by Reverse Transcription were pre-amplified in a 20 µl reaction mix according to the manufacturer's protocol. Following pre-amplification, miRNA-cDNA probes were diluted in RNAse free water (1:3, final volume 60 µl) for subsequent PCR analysis and stored at 4° C.

Quantitative Realtime-PCR

MiRNA expression levels were determined by quantitative realtime-PCR applying TaqMan® MicroRNA Assays (#4427975, Applied Biosystems®). 1 µl miRNA-cDNA per sample was used in a total reaction volume of 10 µl according to the manufacturer's protocol on Mastercycler® ep Realplex (Eppendorf AG, Hamburg, Germany). Relative quantification of different miRNA types resulted from $\Delta C_t$ method normalized on corresponding median expression values of housekeeping miRNAs miR-16 and miR-26b. Data acquisition is based upon mean values of duplicate PCR analysis.

Results

As an essential prior condition for reliable miRNA quantification analysis in urine, the expression levels of various miRNA types were investigated in regard to their potential role as solid housekeeping genes (HKG) in this clinical study. Since robust housekeepers of tissue-based miRNA analyses (e.g. snRNA U) had to be excluded in advance, our preliminary qPCR-based scanning procedure could identify miR-16 and mir-26b as potential candidates. Among the potential HKGs within the range offered by supplier (ABI), expression data analysis was performed applying 'BestKeeper', an Excel-based tool using pair-wise correlations for the determination of stable housekeeping genes, differentially regulated target genes and sample integrity [25]. The assays and subsequent data analysis demonstrated that miR-16 and miR-26b were characterized by stable and consistent expression values in a set of >50 urine specimen—independent of origin from BC patients or healthy controls (BestKeeper; miR-16: p=0.001; miR-26b: p=0.001). These results indicate miR-16 and miR-26b in urine as the best internal control for normalization in this experimental approach.

These two miRNAs were already implemented as HKG in different contexts of miRNA expression analyses [10, 11, 26, 27]. In fact, Davoren and colleagues could identify miR-16 and miR-26b as highly ranked suitable housekeeping miRNAs with expression stability calculated from intra- and intergroup variation (NormFinder) and also based on an estimate of pairwise variation (geNorm) [26]. According to current methodological standard procedure in qPCR quantification [28, 29] the geometric mean of miR-16 and miR-26b expression served as comparative value for quantitative assessment of relevant miRNAs in a duplicate analysis.

Figure 5:
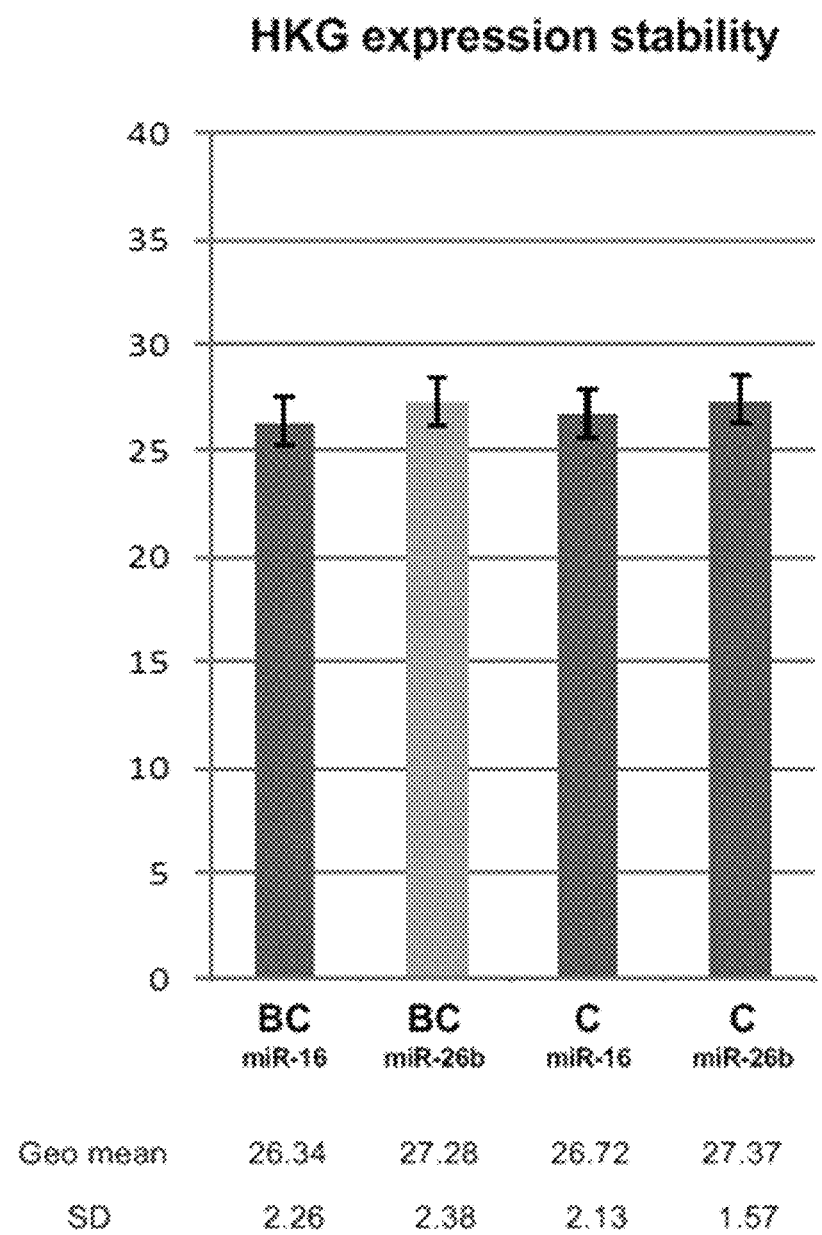
FIG. 5: HKG expression stability in qPCR analysis. Expression values (geometric mean) of housekeeping miR-NAs miR-16 and miR-26b in BC patients (BC) and healthy controls (C). Standard deviation (SD) and numerical values below vertical-bar diagram.
Figure 6A:
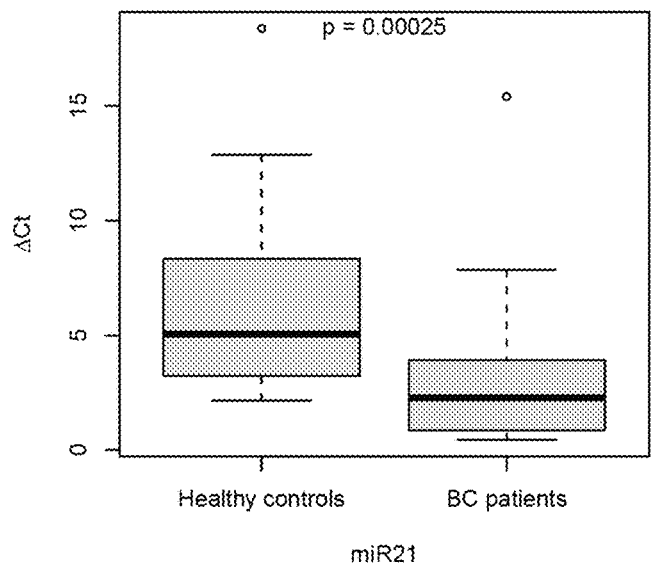
FIGS. 6A to 6I: Box plots A-I of ΔCt-values of all nine investigated urinary miRNAs in breast cancer patients compared to healthy controls. Median urinary expression levels of miR-21, miR-34a, miR-125b, miR-155, miR-195, miR-200b, miR-200c, miR-375, and miR-451. Median ΔCt-value and interquartile range of duplicate experiments. Thick lines: median (50% percentile); gray boxes: 25% to 75% percentile; thin lines: minimal and maximal value, °: moderate outlier. Mann Withney-U test. Quantitative realtime-PCR.
Figure 6B:
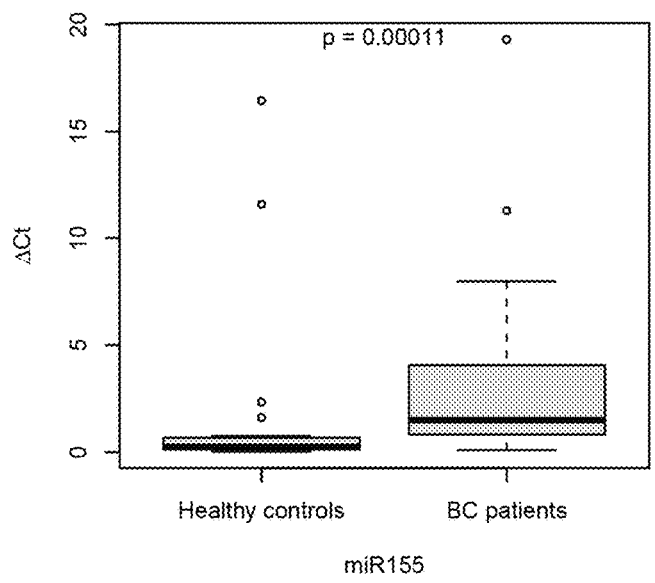
Figure 6C:
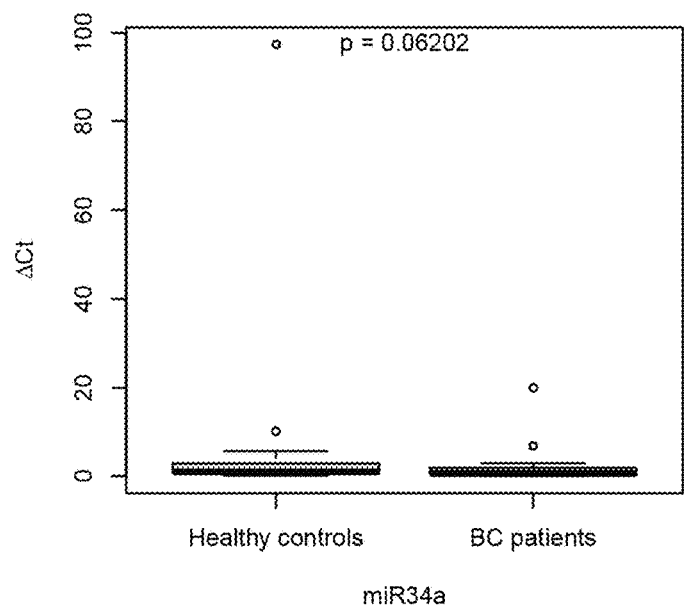
Figure 6D:
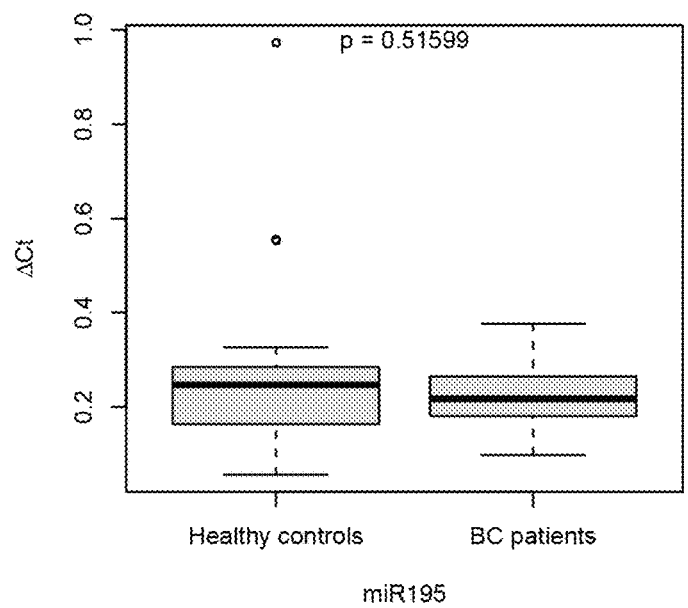
Figure 6E:
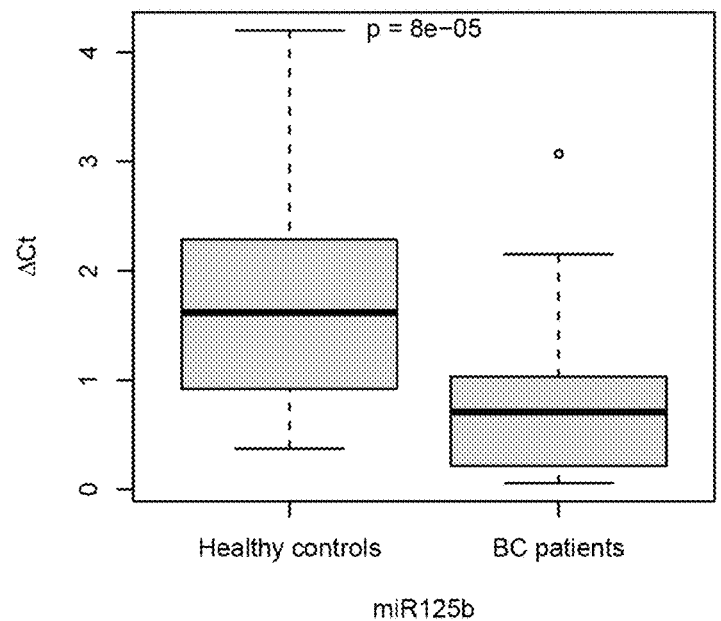
Figure 6F:
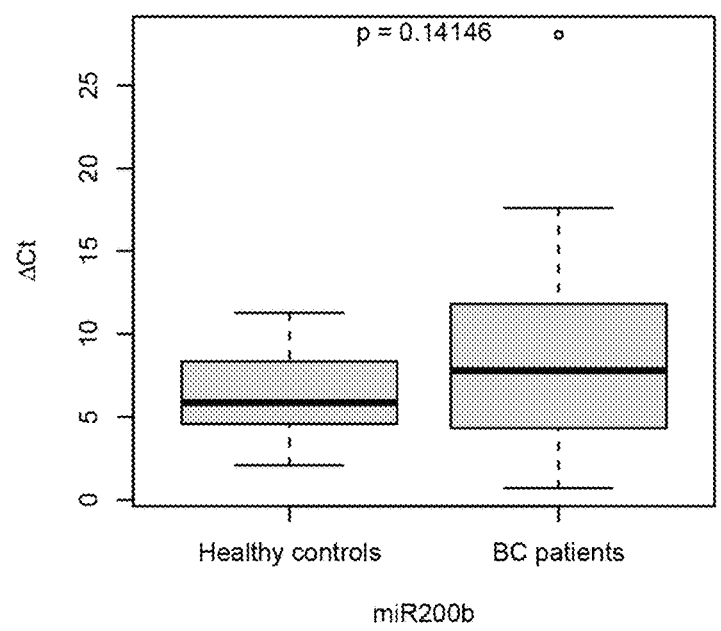
Figure 6G:
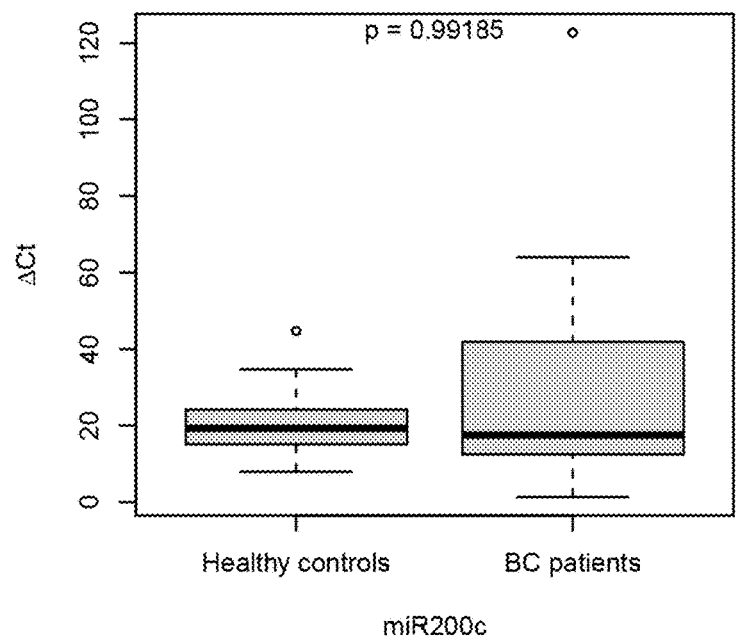
Figure 6H:
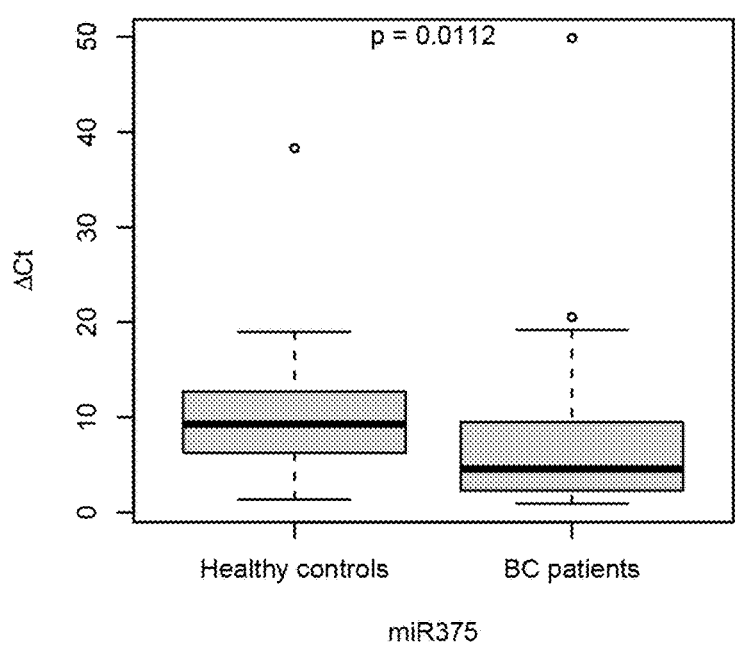
Figure 6I:
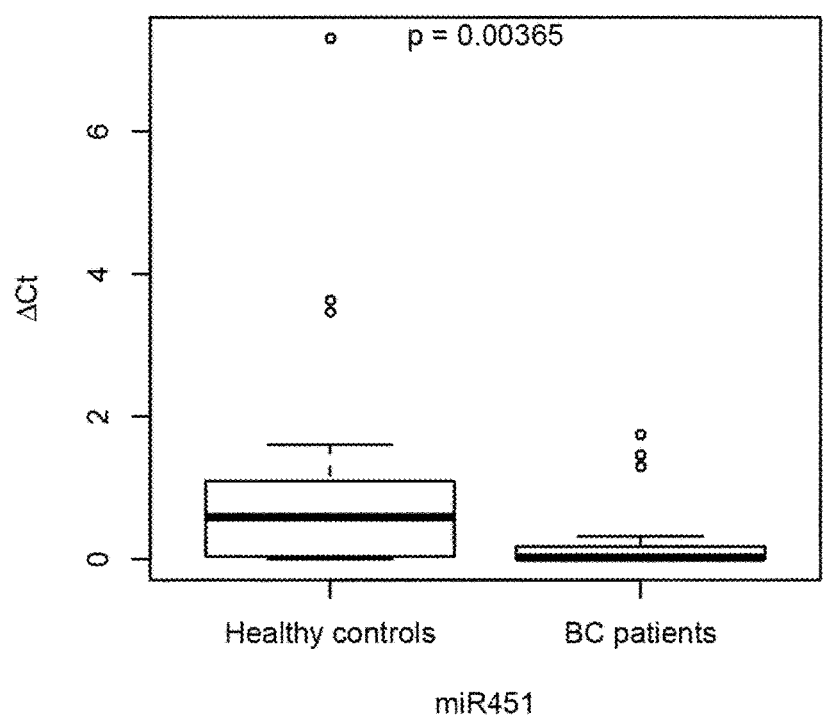

The complete panel of the selected nine miRNAs was detectable in urine by our newly designed qRT-PCR protocol. The findings were reproducible with acceptable inter- and intra-assay variations. Intra-assay standard deviation of corresponding single values in miRNA expression level quantification remained within a range of <0.2%, inter-assay standard deviation within a range of <0.3% (FIG. 4A, FIG. 4B). Expression stability of HKG miR-16 and -26b was determined for both, BC patients and healthy controls (FIG. 5).

The quantification of urinary expression levels of these miRNAs revealed distinct pattern for both, healthy controls and BC patients, respectively. Our data showed significant differences in the expression of four BC associated miRNAs determined as median $\Delta C_t$ values of the distinct miRNA specimen normalized against the geometric mean of the two housekeepers miR-16 and miR-26b, respectively. In detail, urinary miRNA-155 expression was significantly increased in BC patients compared to healthy controls (1.49 vs. 0.25; p<0.001) (table 3; FIGS. 1A to 1D). In contrast, compared to healthy controls, BC patients exhibited significantly lower median urinary expression levels of miR-21, (2.27 vs. 5.07; p<0.001), miR-125b (0.71 vs. 1.62; p<0.001), and miR-451 (0.02 vs. 0.59; p=0.004) (table 3; FIGS. 1A to 1D), respectively. For the additional miRNAs, miR-34a, 195, 200b, 200c, respectively, urinary expression levels did not show any significant differences between BC patients and healthy controls (table 3; FIGS. 6A to 6I). MiR-375 demonstrated a strong tendency towards significant expression differences between BC patients group vs. controls (4.56 vs. 9.29; p=0.011) (table 3; FIGS. 6A to 6I). ROC curve analyses were performed to evaluate the diagnostic power of the selected urinary miRNAs for BC detection. The combined nine miRNAs revealed with an excellent AUC of 0.932, an optimal sensitivity of 0.917 (95%-CI [0.812; 1.000]) as well as specificity of 0.917 (95%-CI [0.686; 0.978]), respectively, the best diagnostic accuracy in discrimination of BC patients from healthy controls (FIG. 2A). A scoring approach employing only the four significantly altered miRNAs (miR-21, miR-125b, miR-155 and miR-451) still revealed a good but lower diagnostic accuracy when compared to the nine miRNA score, with an AUC of 0.887, sensitivity of 0.833 (95%-CI[0.697; 0.997]) and specificity of 0.875 (95%-CI [0.640; 0.957]), respectively (FIG. 2B). In contrast, the accuracy dropped significantly, when the four latter mentioned miRNAs were solitarily analyzed with an AUC ranging from 0.819 to 0.773 (FIGS. 3A-3I).

The comparative subsequent analysis of these miRNA profiles in serum of BC patients (n=4) and healthy controls (n=4) showed no significant differences in median serum levels between the two groups, respectively. In addition the intra-group comparison of urinary to serum miRNA levels in BC patients as well as in healthy controls demonstrated no interrelation between the two different compartments (tables 4-6). Interestingly, all urine samples tested were characterized by miR-375 expression, while corresponding serum samples did not show any detectable miR-375 levels.

TABLE 3

Expression levels of urinary miRNAs of BC patients and healthy controls
Median urinary expression levels of nine breast cancer-related miRNAs in 24 BC patients and 24 healthy controls.
Mann Withney-U test, interquartile range in parentheses.

|  | Median urine level in BC patients | Median urine level in healthy controls | p value |
| --- | --- | --- | --- |
| miR-21 | 2.27 (0.79-4.01) | 5.07 (3.15-8.51) | <0.001 |
| miR-34a | 0.62 (0.29-2.03) | 0.97 (0.69-2.91) | 0.061 |
| miR-125b | 0.71 (0.21-1.07) | 1.62 (0.91-2.29) | <0.001 |
| miR-155 | 1.49 (0.80-4.58) | 0.25 (0.12-0.71) | <0.001 |
| miR-195 | 0.22 (0.18-0.27) | 0.25 (0.16-0.29) | 0.509 |
| miR-200b | 7.78 (4.24-12.20) | 5.86 (4.57-8.50) | 0.138 |
| miR-200c | 17.47 (12.38-44.07) | 19.26 (14.49-24.49) | 0.984 |
| miR-375 | 4.56 (2.25-9.81) | 9.29 (6.24-12.80) | 0.011 |
| miR-451 | 0.02 (0-0.22) | 0.59 (0.04-1.13) | 0.004 |

TABLE 4

Comparison of miRNA expression levels in serum of BC patients and controls

|  | Median serum level in BC patients | Median serum level in healthy controls | p value |
| --- | --- | --- | --- |
| miR-21 | 0.037 (0.023-0.061) | 0.052 (0.043-0.070) | 0.248 |
| miR-34a | 0.0000 (0.0000-0.0007) | n.e. |  |
| miR-125b | 0.004 (0.0017-0.0047) | 0.0055 (0.004-0.011) | 0.189 |
| miR-155 | 0.0805 (0.0697-0.122) | 0.0910 (0.056-0.123) | 0.773 |
| miR-195 | 0.4820 (0.3492-0.4970) | 0.4525 (0.4385-0.4627) | 0.245 |
| miR-200b | 0.0010 (0.00025-0.0010) | 0.0010 (0.00025-0.0010) | 1.000 |
| miR-200c | 0.0050 (0.0035-0.0057) | 0.0045 (0.0040-0.0050) | 1.000 |
| miR-375 | n.e. |  |  |
| miR-451 | 14.704 (12.279-16.514) | 16.195 (11.986-18.881) | 0.564 |

TABLE 5

Comparison of miRNA expression levels in serum and in urine of BC patients

|  | Median serum level in BC patients | Median urine level in BC patients | p value |
| --- | --- | --- | --- |
| miR-21 | 0.037 (0.023-0.061) | 2.519 (2.206-3.735) | 0.021 |
| miR-34a | 0.0000 (0.0000-0.0007) | 0.4351 (0.2969-0.5947) | 0.018 |
| miR-125b | 0.004 (0.0017-0.0047) | 0.9104 (0.8781-0.9469) | 0.020 |
| miR-155 | 0.0805 (0.0697-0.122) | 0.8287 (0.5081-1.1731) | 0.021 |
| miR-195 | 0.4820 (0.3492-0.4970) | 0.1492 (0.1131-0.1825) | 0.020 |
| miR-200b | 0.0010 (0.00025-0.0010) | 5.8679 (3.9532-5.8679) | 0.018 |
| miR-200c | 0.0050 (0.0035-0.0057) | 12.3408 (8.1238-15.9909) | 0.020 |
| miR-375 | n.e. | 4.6812 (2.6637-7.9188) | 0.014 |
| mir-451 | 14.704 (12.279-16.514) | 0.0337 (0.0088-0.2125) | 0.021 |

TABLE 6

Comparison of miRNA expression levels in serum and in urine of controls

| | Median serum level in healthy controls | Median urine level in healthy controls | P value |
|---|---|---|---|
| miR-21 | 0.052 (0.043-0.070) | 2.937 (2.3388-3.33379) | 0.021 |
| miR-34a | n.e. | 0.8803 (0.4586-1.0819) | 0.014 |
| miR-125b | 0.0055 (0.004-0.011) | 0.9221 (0.8903-1.1966) | 0.021 |
| miR-155 | 0.0910 (0.056-0.123) | 0.2819 (0.1109-0.6584) | 0.083 |
| miR-195 | 0.4525 (0.4385-0.4627) | 0.2515 (0.1786-0.2661) | 0.021 |
| miR-200b | 0.0010 (0.00025-0.0010) | 6.9889 (5.6739-7.7862) | 0.018 |
| miR-200c | 0.0045 (0.0040-0.0050) | 18.8527 (17.3459-21.2209) | 0.019 |
| miR-375 | n.e. | 11.1527 (6.6177-16.3017) | 0.014 |
| mir-451 | 16.195 (11.986-18.881) | 0.9886 (0.2645-1.0246) | 0.020 |

ABBREVIATIONS

AUC=area under the curve
Bak1=Bcl-2 antagonist killer1
BC=breast cancer
cDNA=complementary DNA
DEPC=Diethylpyrocarbonate
ER=estrogen receptor
HKG=housekeeping gene
MDR1/P-glycoprotein=Multidrug resistance-1/P-glycoprotein
miR, miRNA=microRNA
MSU=midstream specimens of urine
PDCD4=Programmed Cell Death 4
PR=Progesterone receptor
PTEN=Phosphatase and tensin homolog
qPCR=quantitative polymerase chain reaction
qRT-PCR=quantitative reverse transcriptase polymerase chain reaction
realtime-PCR=realtime polymerase chain reaction
RNA=ribonucleic acid
ROC=Receiver Operating Characteristic
TPM1=Tropomyosin alpha-1 chain

REFERENCES

1. Lewis B P, Burge C B, Bartel D P: Conserved seed pairing, often flanked by adenosines, indicates that thousands of human genes are microRNA targets. *Cell* 2005, 120(1):15-20.
2. Thorsen S B, Obad S, Jensen N F, Stenvang J, Kauppinen S: The therapeutic potential of microRNAs in cancer. *Cancer J* 2012, 18(3):275-284.
3. Sandhu S, Garzon R: Potential applications of microRNAs in cancer diagnosis, prognosis, and treatment. *Semin Oncol* 2011, 38(6):781-787.
4. Mulrane L, McGee S F, Gallagher W M, O'Connor D P: miRNA dysregulation in breast cancer. *Cancer Res* 2013, 73(22):6554-6562.
5. Jung M, Schaefer A, Steiner I, Kempkensteffen C, Stephan C, Erbersdobler A, Jung K: Robust microRNA stability in degraded RNA preparations from human tissue and cell samples. *Clin Chem* 2010, 56(6):998-1006.
6. Mattie M D, Benz C C, Bowers J, Sensinger K, Wong L, Scott G K, Fedele V, Ginzinger D, Getts R, Haqq C: Optimized high-throughput microRNA expression profiling provides novel biomarker assessment of clinical prostate and breast cancer biopsies. *Molecular cancer* 2006, 5:24.
7. Turchinovich A, Weiz L, Langheinz A, Burwinkel B: Characterization of extracellular circulating microRNA. *Nucleic Acids Res* 2011, 39(16):7223-7233.
8. Ajit S K: Circulating microRNAs as biomarkers, therapeutic targets, and signaling molecules. *Sensors (Basel)* 2012, 12(3):3359-3369.
9. Mlcochova H, Hezova R, Stanik M, Slaby O: Urine microRNAs as potential noninvasive biomarkers in urologic cancers. *Urol Oncol* 2014, 32(1):41 e41-49.
10. Asaga S, Kuo C, Nguyen T, Terpenning M, Giuliano A E, Hoon D S: Direct serum assay for microRNA-21 concentrations in early and advanced breast cancer. *Clin Chem* 2011, 57(1):84-91.
11. Roth C, Rack B, Muller V, Janni W, Pantel K, Schwarzenbach H: Circulating microRNAs as blood-based markers for patients with primary and metastatic breast cancer. *Breast cancer research: BCR* 2010, 12(6): R90.
12. Cortez M A, Bueso-Ramos C, Ferdin J, Lopez-Berestein G, Sood A K, Calin G A: MicroRNAs in body fluids—the mix of hormones and biomarkers. *Nat Rev Clin Oncol* 2011, 8(8):467-477.
13. Heneghan H M, Miller N, Lowery A J, Sweeney K J, Newell J, Kerin M J: Circulating microRNAs as novel minimally invasive biomarkers for breast cancer. *Ann Surg* 2010, 251(3):499-505.
14. Wu X, Somlo G, Yu Y, Palomares M R, Li A X, Zhou W, Chow A, Yen Y, Rossi J J, Gao H et al: De novo sequencing of circulating miRNAs identifies novel markers predicting clinical outcome of locally advanced breast cancer. *J Transl Med* 2012, 10:42.
15. Petrovic N, Mandusic V, Stanojevic B, Lukic S, Todorovic L, Roganovic J, Dimitrijevic B: The difference in miR-21 expression levels between invasive and noninvasive breast cancers emphasizes its role in breast cancer invasion. *Medical oncology* 2014, 31(3):867.
16. Chen J, Wang X: MicroRNA-21 in breast cancer: diagnostic and prognostic potential. *Clinical & translational oncology: official publication of the Federation of Spanish Oncology Societies and of the National Cancer Institute of Mexico* 2014, 16(3):225-233.
17. Zhao F L, Dou Y C, Wang X F, Han D C, Lv Z G, Ge S L, Zhang Y K: Serum microRNA-195 is down-regulated in breast cancer: a potential marker for the diagnosis of breast cancer. *Molecular biology reports* 2014, 41(9): 5913-5922.
18. Heneghan H M, Miller N, Kelly R, Newell J, Kerin M J: Systemic miRNA-195 differentiates breast cancer from other malignancies and is a potential biomarker for detecting noninvasive and early stage disease. *Oncologist* 2010, 15(7):673-682.
19. Mattiske S, Suetani R J, Neilsen P M, Callen D F: The oncogenic role of miR-155 in breast cancer. *Cancer epidemiology, biomarkers & prevention: a publication of* the American Association for Cancer Research, cosponsored by the American Society of Preventive Oncology 2012, 21(8):1236-1243.
20. Sochor M, Basova P, Pesta M, Dusilkova N, Bartos J, Burda P, Pospisil V, Stopka T: Oncogenic MicroRNAs: miR-155, miR-19a, miR-181b, and miR-24 enable monitoring of early breast cancer in serum. *BMC cancer* 2014, 14:448.
21. Pecot C V, Rupaimoole R, Yang D, Akbani R, Ivan C, Lu C, Wu S, Han H D, Shah M Y, Rodriguez-Aguayo C et al: Tumour angiogenesis regulation by the miR-200 family. *Nature communications* 2013, 4:2427.
22. Bojmar L, Karlsson E, Ellegard S, Olsson H, Bjornsson B, Hallbook O, Larsson M, Stal O, Sandstrom P: The role of microRNA-200 in progression of human colorectal and breast cancer. *PloS one* 2013, 8(12):e84815.
23. Madhavan D, Zucknick M, Wallwiener M, Cuk K, Modugno C, Scharpff M, Schott S, Heil J, Turchinovich A, Yang R et al: Circulating miRNAs as surrogate markers for circulating tumor cells and prognostic markers in metastatic breast cancer. *Clin Cancer Res* 2012, 18(21): 5972-5982.
24. Ng E K, Li R, Shin V Y, Jin H C, Leung C P, Ma E S, Pang R, Chua D, Chu K M, Law W L et al: Circulating microRNAs as specific biomarkers for breast cancer detection. *PloS one* 2013, 8(1):e53141.
25. Pfaffl M W, Tichopad A, Prgomet C, Neuvians T P: Determination of stable housekeeping genes, differentially regulated target genes and sample integrity: Best-Keeper—Excel-based tool using pair-wise correlations. *Biotechnology letters* 2004, 26(6):509-515.
26. Davoren P A, McNeill R E, Lowery A J, Kerin M J, Miller N: Identification of suitable endogenous control genes for microRNA gene expression analysis in human breast cancer. *BMC molecular biology* 2008, 9:76.
27. Brase J C, Wuttig D, Kuner R, Sultmann H: Serum microRNAs as non-invasive biomarkers for cancer. *Molecular cancer* 2010, 9:306.
28. Vandesompele J, De Preter K, Pattyn F, Poppe B, Van Roy N, De Paepe A, Speleman F: Accurate normalization of real-time quantitative RT-PCR data by geometric averaging of multiple internal control genes. *Genome biology* 2002, 3(7):RESEARCH0034.
29. Mestdagh P, Van Vlierberghe P, De Weer A, Muth D, Westermann F, Speleman F, Vandesompele J: A novel and universal method for microRNA RT-qPCR data normalization. *Genome biology* 2009, 10(6): R64.
30. Wang H, Tan G, Dong L, Cheng L, Li K, Wang Z, Luo H: Circulating MiR-125b as a marker predicting chemoresistance in breast cancer. *PloS one* 2012, 7(4): e34210.
31. Mar-Aguilar F, Mendoza-Ramirez J A, Malagon-Santiago I, Espino-Silva P K, Santuario-Facio S K, Ruiz-Flores P, Rodriguez-Padilla C, Resendez-Perez D: Serum circulating microRNA profiling for identification of potential breast cancer biomarkers. *Dis Markers* 2013, 34(3):163-169.
32. Faraoni I, Antonetti F R, Cardone J, Bonmassar E: miR-155 gene: a typical multifunctional microRNA. *Biochim Biophys Acta* 2009, 1792(6):497-505.
33. Yan L X, Huang X F, Shao Q, Huang M Y, Deng L, Wu Q L, Zeng Y X, Shao J Y: MicroRNA miR-21 overexpression in human breast cancer is associated with advanced clinical stage, lymph node metastasis and patient poor prognosis. *Rna* 2008, 14(11):2348-2360.
34. Iorio M V, Ferracin M, Liu C G, Veronese A, Spizzo R, Sabbioni S, Magri E, Pedriali M, Fabbri M, Campiglio M et al: MicroRNA gene expression deregulation in human breast cancer. *Cancer Res* 2005, 65(16):7065-7070.
35. Christodoulatos G S, Dalamaga M: Micro-RNAs as clinical biomarkers and therapeutic targets in breast cancer: Quo vadis? *World journal of clinical oncology* 2014, 5(2):71-81.
36. Zhu S, Si M L, Wu H, Mo Y Y: MicroRNA-21 targets the tumor suppressor gene tropomyosin 1 (TPM1). *J Biol Chem* 2007, 282(19):14328-14336.
37. Frankel L B, Christoffersen N R, Jacobsen A, Lindow M, Krogh A, Lund A H: Programmed cell death 4 (PDCD4) is an important functional target of the microRNA miR-21 in breast cancer cells. *J Biol Chem* 2008, 283(2):1026-1033.
38. Madhavan D, Cuk K, Burwinkel B, Yang R: Cancer diagnosis and prognosis decoded by blood-based circulating microRNA signatures. *Front Genet* 2013, 4:116.
39. Zhu H, Wu H, Liu X, Evans B R, Medina D J, Liu C G, Yang J M: Role of MicroRNA miR-27a and miR-451 in the regulation of MDR1/P-glycoprotein expression in human cancer cells. *Biochem Pharmacol* 2008, 76(5): 582-588.
40. Weber J A, Baxter D H, Zhang S, Huang D Y, Huang K H, Lee M J, Galas D J, Wang K: The microRNA spectrum in 12 body fluids. *Clin Chem* 2010, 56(11):1733-1741.
41. Cheng L, Sun X, Scicluna B J, Coleman B M, Hill A F: Characterization and deep sequencing analysis of exosomal and non-exosomal miRNA in human urine. *Kidney international* 2013.
42. Mizuta K, Awazu S, Yasuda T, Kishi K: Purification and characterization of three ribonucleases from human kidney: comparison with urine ribonucleases. *Archives of biochemistry and biophysics* 1990, 281(1):144-151.
43. Spencer J D, Schwaderer A L, Dirosario J D, McHugh K M, McGillivary G, Justice S S, Carpenter A R, Baker P B, Harder J, Hains D S: Ribonuclease 7 is a potent antimicrobial peptide within the human urinary tract. *Kidney international* 2011, 80(2):174-180.
44. Roma-Rodrigues C, Fernandes A R, Baptista P V: Exosome in Tumour Microenvironment: Overview of the Crosstalk between Normal and Cancer Cells. *BioMed research international* 2014, 2014:179486.
45. Rana S, Malinowska K, Zoller M: Exosomal tumor microRNA modulates premetastatic organ cells. *Neoplasia* 2013, 15(3):281-295.
46. Hannafon B N, Ding W Q: Intercellular Communication by Exosome-Derived microRNAs in Cancer. *International journal of molecular sciences* 2013, 14(7):14240-14269.
47. Chan M, Liaw C S, Ji S M, Tan H H, Wong C Y, Thike A A, Tan P H, Ho G H, Lee A S: Identification of circulating microRNA signatures for breast cancer detection. *Clin Cancer Res* 2013, 19(16):4477-4487.
48. Gong C, Yao Y, Wang Y, Liu B, Wu W, Chen J, Su F, Yao H, Song E: Up-regulation of miR-21 mediates resistance to trastuzumab therapy for breast cancer. *J Biol Chem* 2011, 286(21):19127-19137.
49. Si H, Sun X, Chen Y, Cao Y, Chen S, Wang H, Hu C: Circulating microRNA-92a and microRNA-21 as novel minimally invasive biomarkers for primary breast cancer. *J Cancer Res Clin Oncol* 2013, 139(2):223-229.
50. Kastl L, Brown I, Schofield A C: miRNA-34a is associated with docetaxel resistance in human breast cancer cells. *Breast cancer research and treatment* 2012, 131(2): 445-454.
51. Scott G K, Goga A, Bhaumik D, Berger C E, Sullivan C S, Benz C C: Coordinate suppression of ERBB2 and ERBB3 by enforced expression of micro-RNA miR-125a or miR-125b. *J Biol Chem* 2007, 282(2):1479-1486.
52. Sun Y, Wang M, Lin G, Sun S, Li X, Qi J, Li J: Serum microRNA-155 as a potential biomarker to track disease in breast cancer. *PloS one* 2012, 7(10):e47003.
53. Johansson J, Berg T, Kurzejamska E, Pang M F, Tabor V, Jansson M, Roswall P, Pietras K, Sund M, Religa P et al: MiR-155-mediated loss of C/EBPbeta shifts the TGF-beta response from growth inhibition to epithelial-mesenchymal transition, invasion and metastasis in breast cancer. *Oncogene* 2013, 32(50):5614-5624.
54. Li X, Roslan S, Johnstone C N, Wright J A, Bracken C P, Anderson M, Bert A G, Selth L A, Anderson R L, Goodall G J et al: MiR-200 can repress breast cancer metastasis through ZEB1-independent but moesin-dependent pathways. *Oncogene* 2013.
55. Gregory P A, Bert A G, Paterson E L, Barry S C, Tsykin A, Farshid G, Vadas M A, Khew-Goodall Y, Goodall G J: The miR-200 family and miR-205 regulate epithelial to mesenchymal transition by targeting ZEB1 and SIP1. *Nat Cell Biol* 2008, 10(5):593-601.
56. Bergamaschi A, Katzenellenbogen B S: Tamoxifen downregulation of miR-451 increases 14-3-3zeta and promotes breast cancer cell survival and endocrine resistance. *Oncogene* 2012, 31(1):39-47.

What is claimed:

1. A method of diagnosing a subject with breast cancer, said method comprising the steps of:
   a. detecting and measuring the levels of the following four miR gene products: miR-21, miR125b, miR-451, and miR-155 in a cell-free test sample isolated from a whole urine sample obtained from said subject;
   b. comparing the respective levels of each of said four miR gene products in the subject test sample detected and measured in step (a) with its corresponding miR gene product control level in a control sample; and
   c. diagnosing with breast cancer the subject for whom the comparison of step (b) reveals a decrease in the respective levels of miR-21, miR-125b, and miR-451, and an increase in the level of miR-155 in the subject test sample measured in step (a) as compared to each corresponding control level,
   wherein said cell-free test sample is a supernatant isolated from the whole urine sample, wherein the whole urine sample has been processed to eradicate contamination with any urothelial or microbiological cell material.

2. The method of claim 1, wherein said subject test sample is contacted with (i) an oligonucleotide capable of hybridizing under high stringency conditions to a nucleic acid consisting of SEQ ID NO:1, (ii) an oligonucleotide capable of hybridizing under high stringency conditions to a nucleic acid consisting of SEQ ID NOs: 3 or 9; (iii) an oligonucleotide capable of hybridizing under high stringency conditions to a nucleic acid consisting of SEQ ID NO: 5; and (iv) an oligonucleotide capable of hybridizing under high stringency conditions to a nucleic acid consisting of SEQ ID NO: 7.

3. The method of claim 1, wherein the levels of each of said four miR gene products are measured by quantitative RT-PCR.

4. The method of claim 1, wherein the levels of each of said four miR gene products are measured by hybridization using an oligonucleotide microarray.

5. The method of claim 4, wherein said oligonucleotide microarray comprises:
   a. an oligonucleotide capable of hybridizing under high stringency conditions with a nucleic acid consisting of SEQ ID NO: 2;
   b. an oligonucleotide capable of hybridizing under high stringency conditions with a nucleic acid consisting of SEQ ID NO: 4;
   c. an oligonucleotide capable of hybridizing under high stringency conditions with a nucleic acid consisting of SEQ ID NO: 6; and
   d. an oligonucleotide capable of hybridizing under high stringency conditions with a nucleic acid consisting of SEQ ID NO: 8.

6. The method of claim 4, wherein said oligonucleotide microarray comprises:
   a. an oligonucleotide perfectly complementary to a nucleic acid consisting of SEQ ID NO: 2;
   b. an oligonucleotide perfectly complementary to a nucleic acid consisting of SEQ ID NO: 4;
   c. an oligonucleotide perfectly complementary to a nucleic acid consisting of SEQ ID NO: 6; and
   d. an oligonucleotide perfectly complementary to a nucleic acid consisting of SEQ ID NO: 8.

7. The method of claim 1, wherein the control sample is a urine sample obtained from one or more healthy, cancer-free individuals.

8. The method of claim 1, wherein the subject is a female human.

9. The method of claim 1, wherein the levels of the at least three each of said four miR gene products are measured by hybridization using an oligonucleotide microarray that comprises:
   a. an oligonucleotide capable of hybridizing under high stringency conditions with a nucleic acid consisting of SEQ ID NO: 2;
   b. an oligonucleotide capable of hybridizing under high stringency conditions with a nucleic acid consisting of SEQ ID NO: 4;
   c. an oligonucleotide capable of hybridizing under high stringency conditions with a nucleic acid consisting of SEQ ID NO: 6;
   d. an oligonucleotide capable of hybridizing under high stringency conditions with a nucleic acid consisting of SEQ ID NO: 8.

10. The method of claim 1, wherein the levels of the at-least-three each of said four miR gene products are measured by hybridization using an oligonucleotide microarray, further wherein said oligonucleotide microarray comprises at least three of the following:
    a. an oligonucleotide perfectly complementary to a nucleic acid consisting of SEQ ID NO: 2;
    b. an oligonucleotide perfectly complementary to a nucleic acid consisting of SEQ ID NO: 4;
    c. an oligonucleotide perfectly complementary to a nucleic acid consisting of SEQ ID NO: 6; and
    d. an oligonucleotide perfectly complementary to a nucleic acid consisting of SEQ ID NO: 8.

11. The method of claim 1, wherein said step c) of diagnosing said subject with breast cancer requires a decrease of 25% or more in the level of the miR-21 gene product, the miR-125b gene product, and the miR-451 gene product in the subject test sample, relative to the respective control levels of the corresponding gene products, coupled with an increase of 25% of more in the level of the miR-155 gene product in the subject test sample, relative to the control level of the miR-155 gene product.

12. The method of claim 1, wherein said step c) of diagnosing said subject with breast cancer requires that:
    a. the level of the miR-21 gene product in the test sample from the subject is less than 70% of the level of miR-21 gene product in the control sample;
    b. the level of the miR-125 b gene product in the test sample from the subject is less than 70% of the level of miR-125b gene product in the control sample;
    c. the level of the miR-451 gene product in the test sample from the subject is less than 60% of the level of miR-451 gene product in the control sample;
    d. the level of the miR-155 gene product in the test sample from the subject is more than 300% of the level of miR-155 gene product in the control sample.

13. A method of treating breast cancer in a subject in need thereof, said method comprising the steps of:
    a. in a cell free test sample isolated from a whole urine sample obtained from the subject, detecting and measuring the respective levels of the following four miR gene products: miR-21, miR-125b, miR-451, and miR-155;
    b. comparing the levels of each of said four miR gene products in the subject test sample measured in step (a) with its corresponding miR gene product control level in a control sample; and
    c. administering a chemotherapeutic regimen suitable for treating breast cancer to the subject for whom the comparison of step (b) reveals a decrease in the level of the miR-21 gene product, the miR-125b gene product, and the miR-451 gene product in the subject test sample, relative to the corresponding control level for the respective gene product(s) and reveals an increase in the level of the miR-155 gene product in the subject test sample, relative to the corresponding control level for the respective gene product(s),
    wherein said cell-free test sample is a supernatant isolated from the whole urine sample, wherein the whole urine sample has been processed to eradicate contamination with any urothelial or microbiological cell material.

14. The method of claim 1, wherein the levels of each of said four miR gene products are measured by hybridization using an oligonucleotide microarray comprising at least four probe oligonucleotides, each of which is specific for one of said four miR gene products.

15. The method of claim 1, wherein said supernatant is isolated from said whole urine sample by means of centrifugation.

16. The method of claim 13, further comprising the step of repeating method steps (a) and (b) at regular time intervals in those subjects administered a chemotherapeutic regimen suitable for breast cancer in accordance with step (c) in order to monitor the effectiveness of said chemotherapeutic regimen, wherein an increase in the level of one or more miR gene products selected from the group consisting of miR-21, miR-125b and miR-451 and a decrease in the level of the miR-155 gene product in a test sample isolated from a urine sample obtained from said subject as compared to the initial values determined is indicative of therapeutic success.

* * * * *

SEQUENCE LISTING

```
<160> NUMBER OF SEQ ID NOS: 11

<210> SEQ ID NO 1
<211> LENGTH: 72
<212> TYPE: RNA
<213> ORGANISM: Homo sapiens

<400> SEQUENCE: 1
ugucggguag cuuaucagac ugauguugac uguugaaucu cauggcaaca ccagucgaug      60
ggcugucuga ca                                                         72

<210> SEQ ID NO 2
<211> LENGTH: 22
<212> TYPE: RNA
<213> ORGANISM: Homo sapiens

<400> SEQUENCE: 2
uagcuuauca gacugauguu ga                                              22

<210> SEQ ID NO 3
<211> LENGTH: 88
<212> TYPE: RNA
<213> ORGANISM: Homo sapiens

<400> SEQUENCE: 3
ugcgcuccuc ucaguccug agacccuaac uugugauguu uaccguuuaa auccacgggu      60
uaggcucuug ggagcugcga gucgugcu                                        88

<210> SEQ ID NO 4
<211> LENGTH: 22
<212> TYPE: RNA
<213> ORGANISM: Homo sapiens

<400> SEQUENCE: 4
ucccugagac ccuaacuugu ga                                              22

<210> SEQ ID NO 5
<211> LENGTH: 72
<212> TYPE: RNA
<213> ORGANISM: Homo sapiens

<400> SEQUENCE: 5
cuugggaaug gcaaggaaac cguuaccauu acugaguuua guaaugguaa ugguucucuu      60
gcuauaccca ga                                                         72

<210> SEQ ID NO 6
<211> LENGTH: 22
<212> TYPE: RNA
```

```
<213> ORGANISM: Homo sapiens

<400> SEQUENCE: 6
aaaccguuac cauuacugag uu                                              22

<210> SEQ ID NO 7
<211> LENGTH: 65
<212> TYPE: RNA
<213> ORGANISM: Homo sapiens

<400> SEQUENCE: 7
cuguuaaugc uaaucgugau agggguuuuu gccuccaacu gacuccuaca uauuagcauu      60
aacag                                                                 65

<210> SEQ ID NO 8
<211> LENGTH: 23
<212> TYPE: RNA
<213> ORGANISM: Homo sapiens

<400> SEQUENCE: 8
uuaaugcuaa ucgugauagg ggu                                             23

<210> SEQ ID NO 9
<211> LENGTH: 89
<212> TYPE: RNA
<213> ORGANISM: Homo sapiens

<400> SEQUENCE: 9
accagacuuu uccuagaccc ugagacccua acuugugagg uauuuuagua acaucacaag      60
ucaggcucuu gggaccuagg cggagggga                                       89

<210> SEQ ID NO 10
<211> LENGTH: 64
<212> TYPE: RNA
<213> ORGANISM: Homo sapiens

<400> SEQUENCE: 10
ccccgcgacg agccccucgc acaaaccgga ccugagcguu uuguucguuc ggcucgcgug      60
aggc                                                                  64

<210> SEQ ID NO 11
<211> LENGTH: 22
<212> TYPE: RNA
<213> ORGANISM: Homo sapiens

<400> SEQUENCE: 11
uuuguucguu cggcucgcgu ga                                              22
```